United States Patent [19]

Cotrel et al.

[11] Patent Number: 4,642,308
[45] Date of Patent: Feb. 10, 1987

[54] N-(1,8-NAPHTHYRIDIN-2-YL) AMIDES AND THEIR PHARMACEUTICAL USE

[75] Inventors: Claude Cotrel, Paris; Claude Guyon, Saint-Maur-des-Fosses; Gërard Roussel, Soisy-sur-Seine; Gérard Taurand, Creteil, all of France

[73] Assignee: Rhone-Poulenc Sante, Courbevoie, France

[21] Appl. No.: 755,896

[22] Filed: Jul. 17, 1985

[30] Foreign Application Priority Data

Jul. 19, 1984 [FR] France ............................ 84 11442

[51] Int. Cl.⁴ ..................... A61K 31/50; A61K 31/44; C07D 237/24; C07D 471/04
[52] U.S. Cl. .................................. 514/253; 514/300; 514/313; 544/238; 546/122; 546/159; 546/162
[58] Field of Search ........................ 546/122; 544/238; 514/253, 300

[56] References Cited

U.S. PATENT DOCUMENTS 3,389,142 6/1968 Bristol et al. ........................ 546/156
3,624,097 11/1971 Warner et al. ........................ 546/275

FOREIGN PATENT DOCUMENTS 1923047 11/1969 Fed. Rep. of Germany .
1006725 1/1952 France .
8400489 2/1984 PCT Int'l Appl. .
661515 11/1951 United Kingdom ................ 546/122

Primary Examiner—Henry R. Jiles
Assistant Examiner—Bernard I. Dentz

Attorney, Agent, or Firm—Stevens, Davis, Miller & Mosher

[57] ABSTRACT

The invention provides novel substituted amides of formula:

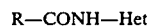

R—CONH—Het in which R is cycloalkyl, cyclohexadienyl, phenyl optionally substituted with one or 2 fluorine atoms or with a hydroxy radical, or substituted at position 3- or 4- with an alkyl or alkyloxy radical, or with a methylenedioxy radical at positions 3- and 4-, or at position 2- or 3- with a dialkylamino radical, or is 3-pyridyl, alkyloxy-3-pyridyl, thienyl, alkylthienyl, furyl, tetrahydropyridyl, pyridazinyl and alkylpyridazinyl, and Het is 2-quinolyl or 1,8-naphthyridin-2-yl, both optionally substituted at position 7- with a halogen atom or a hydroxymethyl, alkyl, alkyloxy, alkyloxyalkyloxy, alkenyloxy or alkynyloxy radical (of 3 or 4 carbon atoms), an alkylthio or benzylthio radical, a phenoxy radical which is optionally substituted (with fluorine, with chlorine or bromine at position 2-, or with an alkyloxy radical or 1 or 2 alkyl radicals) or with pyridyloxy or alkylpiperidyloxy, provided that, when Het is 2-quinolyl, R is other than phenyl, and that the radicals and alkyl portions contain 1 to 4 carbon atoms each in a linear or branched chain.

The new products are useful as anxiolytics, hypnotics, anticonvulsants, antiepileptics and muscle relaxants. The invention also provides a process for the preparation of, and pharmaceutical compositions containing, the new compounds.

11 Claims, No Drawings

N-(1,8-NAPHTHYRIDIN-2-YL) AMIDES AND THEIR PHARMACEUTICAL USE

This invention relates to substituted amides useful in therapy and to their preparation and use.

A wide variety of substituted amides useful in therapy have been described in the literature. For example N-(2-quinolyl)benzamide and its oxide and their preparation have been described by M. A. Solekhova and Yu. V. Kurbatov, Fiz. Khim. Issled. Sintetich. i Prirod Soedine., Samarkand, 10–16 (1980), [C.A. 96 142655 y], M. A. Solekhova and Yu. V. Kurbatov, Zh. Org. Khim., 17 (5), 1121 (1981), [C. A. 95 187028s], and Tamura et al. Chem. Pharm. Bull., 19 (6), 1285–6 (1971).

Benzamide derivatives useful as antiarryhythmics and of the general formula:

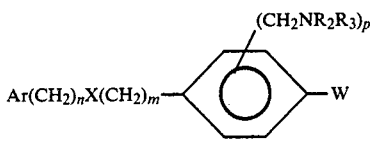

are described in International Patent Application PCT No. 84/00489, 1,8-Naphthyridine derivatives useful as bronochodilators and peripheral vasodilators, or as hypotensive agents, and of the formula:

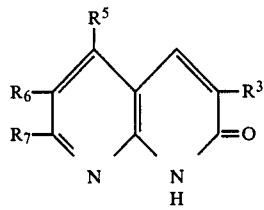

are described in Dutch Patent Application No. 73/05482 and U.S. Pat. No. 3,993,656.

The present invention provides new substituted amides of therapeutic value.

The substituted amides of the present invention have the formula:

R—CONH—Het  (I)

in which R denotes cycloalkyl of 3 to 6 atoms, cyclohexadienyl, phenyl, or phenyl substituted by 1 or 2 fluorine atoms, or by a hydroxy radical, or phenyl substituted at position 3- or 4- by alkyl or alkyloxy, or at positions 3- and 4- by methylenedioxy, or substituted at position 2- or 3- by dialkylamino; or R denotes 3-pyridyl, alkyloxy-3-pyridyl, thienyl, alkylthienyl, furyl, tetrahydropyridyl, pyridazinyl or alkylpyridazinyl; and Het denotes 2-quinolyl or 1,8-naphthyridin-2-yl, each unsubstituted or substituted at position 7- by halogen, hydroxymethyl, alkyl, alkyoxy, alkyloxyalkyloxy. alkenyloxy of 3 to 4 carbon atoms, alkynyloxy of 3 to 4 carbon atoms, alkylthio, benzylthio, phenoxy, phenoxy substituted by fluorine, or by chlorine or bromine at position 2-, or by alkyloxy or by 1 to 2 alkyls, pyridyloxy or alkylpiperidyloxy; provided that, when Het denotes 2-quinolyl, R is other than phenyl, and that the alkyls mentioned above are each linear or branched and contain 1 to 4 carbon atoms. When Het contains a halogen substituent, the latter is fluorine, chlorine or bromine.

According to a feature of the invention, the compounds of formula (I) are prepared by a process which comprises reacting an acid of the formula:

R—COOH  (II)

in which R is as defined above, or a reactive derivative of this acid, with an amine of the formula:

H₂N—Het  (III)

in which Het is as defined above.

When the acid of formula (II) contains a hydroxy radical, the latter is protected beforehand by an known method which does not adversely affect the remainder of the molecule. By way of example, a hydroxyl radical may be protected, in particular, by an acetyl redical which can be removed by treatment with a basic medium, e.g. by treatment with ethanolic caustic potash.

Likewise, when, in the amine of formula (III), the symbol Het contains a hydroxy-alkyl substituent, it is preferable to protect the hydroxy radical prior to the reaction. The protection is performed by an method known per se which does not adversely affect the remainder of the molecule, in particular with a tetrahydropyranyl radical which can be readily eliminated by acidolysis in aqueous medium.

When the acid of general formula (II) is used, the reaction is preferably performed in the presence of a peptide-condensing agent such as a carbodiimide (e.g. dicyclohexylcarbodiimide) or N,N'-carbonyldiimidazole or 2-ethoxy-2-ethoxycarbonyl-1,2-dihydroquinoline, in an organic solvent such as an ether (e.g. tetrahydrofuran, dioxane, ethyleneglycol dimethyl ether (glyme), or diethyleneglycol dimethyl ether (diglyme), an amide (e.g. dimethylformamide), a nitrile (e.g. acetonitrile) or a chlnorinated solvent (e.g. methylene chloride, dichloroethane of chloroform), at a temperature between 0° C. and the reflux temperature of the reaction mixture. The reaction in preferably carried out at about 20° C.

When a reactive derivative of the acid of formula (II) is employed, it is possible to react the anhydride, a mixed anhydride, an acid halide or an ester [which can be an activated or non-activated este of the acid of formula (II)]. The reaction is then performed either in an organic medium, optionally in the presence of an acid acceptor such as a nitrogenous organic base (e.g. a trialkylamine, a pyridine, 1,8-diazabicyclo [5.4.0]undec-7-ene or 1,5-diazabicyclo [4.3.0]non-5-ene, in a solvent as mentioned above, or in a mixture of these solvents, at a temperature between 0° C. and the reflux temperature of the reaction mixture; or in a two-phase aqueous/organic medium in the presence of an alkali metal or alkaline earth metal base (e.g. caustic soda or caustic potash) or a cabonate or bicarbonate of an alakli metal or alkaline earth metal, at a temperature between 0° and 40° C. It is also possible to perform the reaction without a solvent at the melting point of at least one of the ingredients of the reaction mixture.

According to a further feature of the invention, the compounds of formula (I) in which the symbol Het contains a hydroxymethyl substituent are also prepared by reduction of the corresponding aldehyde.

The reduction is advantageously performed by the action of sodium borohydride or by catalytic hydrogenation in the presence of a nickel, platinum or palladium catalyst, in an organic or aqueous/organic medium, e.g. in an alcohol (e.g. methanol or ethanol), in an ether (e.g. tetrahydrofuran or dioxane) or in a mixture of these solvents, at a temperature from 0° to 50° C. The starting aldehyde can be prepared by oxidation of a compound of formula (I) in which Het contains a methyl substituent. This oxdiation may be accomplished with an oxidising agent such as selenium dioxide, in an organic solvent such a dioxane, at the reflux temperature of the reaction mixture.

The acids of formula (II) can be prepared by applying the methods mentioned below (or obvious modifications of them):

H. D. Hartough, The Chemistry of heterocyclic compounds, thiophene and its derivatives, Interscience Publishers Inc. New York, page 363 (1952);

J. W. Mason, the Chemistry of heterocyclic compounds, Pyridazine carboxylic acids, John Wiley and Sons Inc. New York, page 407 (1973);

E. P. Oliveto, The Chemistry of heterocyclic compounds Pyridine-carboxylic acids, Interscience Publishers Inc., Page 179 (1962);

A. A. Petrov, et al., Zhur Obshchei Khim, 26, 1588 (1956), M. E. Kuehne et. al., Org, Synth., 43, 22 (1968), S. Hunig et. al., Chem, Ber., 90, 238 (1957) or H. Plieninger at al., Chem. Ber., 94, 2088 (1961) when the acid in question is a cyclohexadienylcarboxylic acid.

The amines of formula (III) in which the symbol Het bears an alkyloxy, alkyloxyalkyloxy, alkenyloxy, alkynyloxy, alkylthio, benzylthio, unsbustituted or substituted phenoxy, pyridyloxy or alkylpiperidyloxy substituted, can be prepared from the corresponding amine in which the symbol Het bears a halogen substituent (preferably a chlorine atom), by the action, respectively, of a hydroxylated derivative or a thiol of general formulae:

R'OH  (IVa)

or

R"SH  (IVb)

[in which R' denotes an alkyl, alkyloxyalkyl, alkenyl or alkynyl radical, a phenyl radical which is optionally substituted (with a fluorine atom, with a chlorine or bromine atom at position 2-, with an alkyloxy radical or with 1 or 2 alkyl radicals), or a pyridyl or alkylpiperidyl radical, and R" denotes an alkyl or benzyl radical], in basic medium, or by the action of the corresponding alcoholate or thiolate.

The reaction is generally performed in the presence of a strong base (e.g. caustic soda, caustic Potash, quaternary ammonium hydroxide, sodium ethylate), at a temperature between 50° and 150° C., or altenatively in the presence of the alcoholate or corresponding thiolate (e.g. the sodium alcoholate), in a solvent such as an amide (e.g. dimethylformamide) or an ether (e.g. tetrahydrofuran, dimethoxyethane), or without a solvent, in the presence of an excess of hydroxylated derivative or thiol, at a temperature between 70° C. and the reflux temperature of the reaction mixture.

When the alcoholate or thiolate is employed, this is produced beforehand by the action of sodium on the alcohol of general formula (IVa) or the thiol of general formula (IVb), at a temperature between 20° and 80° C., or by the action of sodium hydride at a temperature between 0° and 20° C. in a solvent such a dimethylformamide, dimethoxyethane or tetrahydrofuran. It is not necessary to isolate the alcoholate or thiolate produced to employ it in the following reaction.

The amines of formula (III) in which the symbol Het contains a hydroxymethyl substituent can be produced by reduction of the corresponding aldehyde in which the amine function has been protected beforehand (e.g. by a benzyl radical). The reaction is performed under the conditions described above for preparing a product of formula (I) in which the symbol Het bears a hydroxymethyl substituent. The starting aldehyde also can be prepared by a method similar to the preparation of the starting material in the above process.

The amines of formula (III) can also be prepared by applying the methods described below in the Examples, or by applying the methods described by the following, or obvious modifications of them:

S. Carboni, Gazz. Chim. Italiana, 96, 1456 (1966);

E. V. Brown, J. Org. Chem., 30, 1607 (1965);

E. Jones, The Chemistry of Heterocyclic compounds, Quinolines, John Wiley and Sons Inc., New York, Part I (1977), Part II (1982);

or according to U.S. Pat. Nos. 3,948,917 and 3,884,921.

According to a further feature of the invention, the compounds of formula (1) in which R is a tetrahydropyridyl radical can be prepared by the action of tetrahydropyridine on a carbamate of the formula:

C$_6$H$_5$OCONH—Het  (V)

in which Het is defined as above.

The reaction is generally performed in an organic solvent such as a nitrile (e.g. acetonitrile) or an ether (e.g. tetrahydrofuran), or in a mixture of such solvents, at a temperature between 60° C. and the reflux temperature of the reaction mixture.

The carbamate of formula (V) can be produced by the action of an amine of formula (III) on the corresponding chloroformate.

The procedure is generally performed in pyridine at a temperature between 0° and 40° C., in the presence of an acceptor for acid such as pyridine or a trialkylamine (e.g. triethylamine), optionally in an organic solvent such as tetrahydrofuran.

The compounds of the invention of formula (I) can be purified, where appropriate, by physical methods such as crystallisation or chromatography.

The compounds of formula (I) possess advantageous pharmacological properties. They show a high level of activity as anxiolytics, hypnotics, anti-convulsants, anti-epileptics and muscle relaxants, demonstrated in the tests mentioned below.

More particularly, the new compounds show high affinity in vitro for benzodiazepine receptor sites at concentrations from 5 up to about 1000 nM using the technique described by J. C. Blanchard and L. Julou, J. of Neurochemistry, 40, 601 (1983), which was modelled on the work of Squires and Braestrup, Nature, 266, 732 (1977).

In animals (mice) they have been shown to be active at doses from 10 to about 200 mg/kg orgally, in suppressing convulsions induced by pentrazole using a technique similar to that of Everett and Richards, J. Pharmacol., 81, 402 (1944).

Furthermore, the compounds of formula (I) in which R is a phenyl radical substituted in position 3- or 4- by an alkyl radical or in position 3- and 4- by a methylenedioxy radical and Het is a 1,8-naphthyridin-2-yl radical substituted in position 7- by a radical as defined in the general formula (I), or R is a phenyl radical and Het is a 1,8-naphthyridin-2-yl radical substituted in the 7- position by a hydroxymethyl, alkyl, benzylthio radical or by a substituted phenoxy radical, as defined in the general formula (I), or a pyridyloxy or alkylpiperidyloxy radical, or R is a methoxyphenyl radical and Het is a 1,8-naphthyridin-2-yl radical substituted in position 7- by a bromine atom or a hydroxymethyl, benzylthio or phenoxy radical, show immunostimulant activity.

The immunostimulant activity was demonstrated in vitro at molar concentrations from $10^{-5}$ to $10^{-6}$, by stimulation of the cytostatic activity of mouse peritoneal macrophages in relation to $P_{815}$ tumour cells, using a technique modelled on that of M.I.C. Gyöngyössi et al., Cell. Immunol., 45, 1 (1979), and in vivo, in mice, the same compounds stimulate the defence reactions against *Klebsiella pneumoniae* infection at doses from 2 to 20 mg/kg i.p., using a technique similar to that of M. A. Parant et al., Infect. Immun., 27, 826 (1980).

An advantage of the immunostimulant activity of these new compounds lies in their use an anti-infection agents having, in particular, the ability to combat microorganisms which have been become resistant to traditional antibiotics.

Moreover, the compounds of formula (I) in which R denotes a 4-methoxyphenyl, 3-thienyl or 5-methylthienyl radical and Het deontes a 1,8-naphthyridin-2-yl radical substituted at position 7- with a chlorine atom, a methoxy radical or ahydroxymethyl radical, or alternatively in which R denotes a 2-thienyl radical and Het denotes a 1,8-naphthyridin-2-yl radical substituted at position 7- by a methoxy or phenoxy radical, also show antiviral activity The anitviral activity was demonstrated in vitro on influenzo A and B viruses at concentrations between 1.5 and 30 λg/cc.

Furthermore, these new compounds show in vivo significant protective activity against influenza infection (A2 Am Arbor) in mice, at doses from 30 to 300 mg/kg orally.

The compounds of the invention of formula (I) have low toxicity. Their $LD_{50}$ when given orally in mice is from 300 to 900 mg/kg or in some cases greater than 900 mg/kg.

Especially relevant compounds of formula (I) are those in which R is cyclopropyl or cyclobutyl, 1,4-cyclohexadien-1-yl, phenyl, or phenyl substituted by one or 2 fluorine atoms, or by a hydroxy radical, or substituted at position 3 or 4- by alkyl of 1 or 2 carbon atoms or alkyloxy of 1 to 4 carbon atoms, or at positions 3- and 4-by methylenedioxy, or substituted by dimethylamino at position 3-, or R is 3-pyridyl, 6-alkyloxy-3-pyridyl, thienyl, 5-alkylthienyl, furyl, 3-pyridazinyl or 6-alkyl-3-pyridazinyl in which the alkyl contains 1 or 2 carbon atoms, and Het denotes 2-quinolyl or 1,8-naphthyridin-2-yl unaubstituted or substituted at position 7- by halogen, hydroxymethyl, alkyl or alkylthio of 1 or 2 carbon atoms, alkyloxy of 1 to 4 carbon atoms, alkyloxy of 2 to 4 carbon atoms, allyloxy, proparagyloxy, benzylthio, Phenoxy, phenoxy substituted by fluorine, or by chlorine or bromine in position 2-, by alkyloxy or by 1 or 2 alkyl radicals of 1 or 2 carbon atoms each, 3-pyridyloxy, or 1-alkyl-4-piperidyloxy, provided that, when Het denotes 2-quinolyl, R is other than phenyl.

Among these compounds, the more particularly active compounds of formula (I) are those in which R is cyclopropyl, 1,4-cyclohexadien-1-yl, phenyl, phenyl substituted by 1 or 2 fluorine atoms, or by hydroxy, or substituted at position 3- or 4- by alkyloxy of 1 or 2 carbon atoms, or at positions 3- and 4- by methylenedioxy, or substituted at position 3- by dimethylamino, or R is 3-pyridyl or 6-alkyloxy-3-pyridyl in which the alkyl contains 1 or 2 carbon atoms, thienyl or furyl, and Het denotes a 1,8-naphthyridin-2-yl radical unsubstituted or substituted at position 7by halogen, alkyl, alkyloxy or alkylthio of 1 to 2 carbon atoms, alkyloxyalkyloxy of 2 to 4 carbon atoms, allyloxy, phenoxy, phenoxy substituted by fluorine, or by chlorine or bromine at position 2-, by alkyloxy or by 1 or 2 alkyl radicals of 1 to 2 carbon atoms each, or 3-pyridyloxy.

Especially outstanding compounds of formula (I) are those in which R is cyclopropyl, phenyl, phenyl substituted at position 3- or 4- by fluorine, or substituted by 2 fluorine atoms or by hydroxy, or substituted at position 3- or 4- by methoxy, or R is 6-alkyloxy-3-pyridyl in which the alkyl contains 1 or 2 carbon atoms, 2-theinyl, or 3-furyl, and Het denotes 1,8-naphthyridin-2-yl substituted at position 7- by halogen, methoxy, phenoxy, or phenoxy substituted by a fluorine atom or at position 2- by a chlorine atom or methyl, or at position 2- or 3- by methoxy, or R denotes 1,4-cyclohexadien-1-yl, phenyl substituted at positions 3- and 4- by methylenedioxy or at position 3- by dimethylamino, or 3-pyridyl, and Het denotes 1,8-naphthyridin-2-yl substituted at position 7- by a halogen atom. Specified preferred compounds are:

N-(7-Methoxy-1,8-naphthyridin-2-yl)cyclopropanecarboxamide,

N-(7-Chloro-1,8-naphthyridin-2-yl)-4--fluorobenzamide,

N-(7-Bromo-1,8-naphthyridin -2-yl)-4-methoxybenzamide,

N-(7-Methoxy-1,8-naphthyridin-2-yl)-4-methoxybenzamide, and

N-(7-Methoxy-1,8-naphthyridin-2-yl)-2-thiophenecarboxamide.

The following Examples illustrate the present invention:

EXAMPLE 1

To a solution of p-toluic acid (10.9 g) in 100 cc of anhydrous tetrahydrofuran, N,N'-carbonyldiimidazole (12.9 g) is added. Immediate evolution of a gas is observed. The mixture is stirred for 1 hour at a temperature in the region of 20° C., until the evolution of gas has ceased. 2-Amino-7-chloro-1,8-naphthyridine (8.9 g) is then added and the mixture is heated to reflux for 20 hours. The mixture is poured into distilled water (1000 cc), and the precipitate formed is separated by filtration, washed with water and dried in the air.

The product obtained (13.6 g; m.p. 222° C.) is dissolved in boiling ethanol (470 cc). After 4 hours cooling at 4° C., the crystallised solid is separated by filtration, washed with ethanol (3×20 cc) and dried at 40° C. under reduced pressure (0.067 kPa). N-(7Chloro-1,8-naphthyridin -2-yl)-4-methylbenzamide (10 g) is produced, m.p. 228° C.

EXAMPLE 2

The procedure is similar to that described in Example 1, but starting with a cyclopropylcarboxylic acid (5.2 g , N,N'-carbonyldiimidazole (9.8 g) and 2-amino-7-chloro-1,8-naphthyridine (7.2 g). The product produced by precipitation in water (10 g; m.p. 250° C.) is dissolved in boiling 2-propanol (530 cc).

After 4 hours' cooling at 4° C., the crystallised solid is separated by filtration, washed with 2-propanol (3×20 cc) and dried at 40° C. under reduced pressure (0.067 kPa). N-(7-Chloro-1,8-naphthyridin-2-yl)cyclopropanecarboxamide (7.5 g) is produced, m.p. 250° C.

EXAMPLE 3

The procedure is similar to that described in Example 1, but starting with cyclopropanecarboxylic acid (13.7 g), N,N'-carbonyldiimidazole (25.8 g) and 2-amino-7-methoxy-1,8-naphthyridine (17.5 g). The product produced by precipitation in water (24.3 g; m.p. 100° C.) is purified by chromatography on a column 40 mm in diameter containing silica (400 g; 0.040–0.063 mm), eluting with a mixture (95-5 by volume) of methylene chloride and methanol and collecting 100-cc fractions. After concentration to dryness of fractions 6 to 17 at 40° C. under reduced pressure (4 kPa), a solid (17 g) is produced, m.p. 170° C. This product is dissolved in boiling ethanol (120 cc). After 2 hours' cooling at 4° C., the crystallised solid is separated by filtration, washed with ethanol (2×10 cc) and dried at 40° C. under reduced pressure (0.067 kPa). N-(7-Methoxy-1,8-naphthyridin-2-yl) cyclopropanecarboxamide (12.5 g) are produced, m.p. 170° C.

2-Amino-7-methoxy-1,8-naphthyridine can be prepared according to the method described in U.S. Pat. No. 3,948,917.

EXAMPLE 4

The procedure is similar to that described in Example 1, but starting with cyclopropanecarboxylic acid (4.8 g), N,N'-carbonyldiimidazole (9.07 g) and 2-amino-7-phenoxy-1,8-naphthyridine (10 g). The product produced by precipitation in water (11.2 g; m.p. approximately 170° C.) is dissolved in boiling ethanol (200 cc). After 2 hours' cooling at 4° C., the crystallised solid is separated by filtration, washed with ethanol (2×10 cc) and dried at 40° C. under reduced pressure (0.067 kPa). N-(7-Phenoxy-1,8-naphthyridin-2-yl)cyclopropanecarboxamide (6.4 g) is produced, m.p. 190° C.

2-Amino-7-phenoxy-1,8-naphthyridine can be prepared in the following manner:

A mixture composed of 2-amino-7-chloro-1,8naphthyridine (27 g), phenol (141 g) and potassium hydroxide pellets (19.8 g; 85% purity) is heated for 20 hours at 120° C. The mixture produced is taken up in 4 N aqueous caustic soda solution (300 cc) and extracted with methylene chloride (250 cc).

The aqueous phase is extracted again with methylene chloride (2×200 cc). The organic extracts are washed with 4 N caustic soda (2×150 cc) and then distilled water (250 cc), dried over magnesium sulphate and concentrated to dryness at 40° C. under reduced pressure (4 kPa).

The product produced (30.5 g; m.p. 190°–194° C.) is dissolved in boiling acetonitrile (400 cc). After 2 hours' cooling at 4° C., the crystallised solid is separated by filtration, washed with acetonitrile (20 cc) and dried at 45° C. under reduced pressure (0.067 kPa). 2-Amino-7-phenoxy-1,8-naphthyridine (23.4 g) is produced, m.p. 196° C.

EXAMPLE 5

The procedure is similar to that described in Example 1, but starting with cyclobutanecarboxylic acid (5 g), N,N'-carbonyldiimidazole (10.5 g) and 2-amino-7chloro-1,8-naphthyridine (7 g). The product produced by filtration (9 g; m.p. 192° C.) is dissolved in boiling acetonitrile (150 cc). After 3 hours' cooling at 20° C., the crystallised solid is separated by filtration, washed with ethyl ether (3×25 cc) and dried at 35° C. under reduced pressure (0.066 kPa). N-(7-Chloro-1,8-naphthyridin-2-yl)cyclobutanecarboxamide (6.3 g) is produced, m.p. 192°–194° C. EXAMPLE 6

The procedure is similar to that described in Example 1, but starting with 1,4-cyclohexadiene-1-carboxylic acid (6.2 g), N,N'-carbonyldiimidazole (8 g) and 2-amino-7-chloro-1,8-naphthyridine (8 g). The product produced by precipitation in water (11 g; m.p. 205° C.) is dissolved in boiling ethanol (250 cc). After 2 hours' cooling at 4° C., the crystallised solid is separated by filtration, washed with ethanol (3×15 cc) and dried at 40° C. under reduced pressure (0.067 kPa). N-(7Chloro-1,8-naphthyridin-2-yl)-1,4-cyclohexadiene-1-carboxamide (4.2 g) is produced, m.p. 210° C.

1,4-Cyclohexadiene-1-carboxylic acid can be prepared according to the method described by A. A. Petrov. et al., Zhur Obshchei Khim, 26, 1588 (1956) [C.A. 51 1887e (1957)].

EXAMPLE 7

The procedure is similar to that described in Example 1, but starting with 1,4-cyclohexadiene-1-carboxylic acid (12.4 g), N,N'-carbonyldiimidazole (16.2 g) and 2-amino-7-phenoxy-1,L-naphthyridine (21.4 g). The product obtained by precipitation in water (17.2 g; m.p. 95° D.) is dissolved in boiling methanol (150 cc). After 3 hours' cooling at 20° C., the crystallised solid is separated by filtration, washed with methanol (3×15 cc) and dried at 40° C. under reduced pressure (0.067 kPa). N-(7-phenoxy-1,8-naphthyridin-2-yl)-1,4-cyclo-hexadiene-1car-boxamide (13.2 g) is produced, m.p. 95° C. EXAMPLE 8

To a solution of 2-amino-7-chloro-1,8-naphthyridine (5.4 g) in pyridine (60 cc), benzoyl chloride (4.2 g) is added slowly, maintaining the temperature in the region of 30° C. After the solution has been maintained for 3 hours at a temperature in the region of 20° C., the product is precipitated in distilled water (340 cc). The solid produced after drying in the air is dissolved in boiling ethanol (88 cc). After 3 hours' cooling at 4° C., the crystallised solid is separated by filtration, washed with ethanol (2×5 cc) and dried at 40° C. under reduced pressure (0.067 kPa). N-(7-chloro-1,8-naphthyridin-2-yl)benzamide (4.95 g) is thus produced, m.p. 198° C. EXAMPLE 9

The procedure is similar to that described in Example 1, but starting with benzoic acid (13.4 g), N,N'carbonyldiimidazole (17.8 g) and 2-amino-7-methoxy-1,8naphthyridine (12.3 g). The product produced by precipitation in water (20 g; m.p. 80° C.) is dissolved in boiling acetonitrile (200 cc). After 1 hour's cooling at 4° C., the crystallised solid is separated by filtration, washed with acetonitrile (2×10 cc) and dried at 40° C. under reduced pressure (0.067 kPa). N-(7-methoxy-1,8-naphthyridin-2-yl)benzamide (7.8 g) is produced, m.p. 134° C. EXAMPLE 10

The procedure is similar to that described in Example 1, but starting with benzoic acid (8.9 g), N,N'carbonyldiimidazole (11.8 g) and 2-amino-7-benzylthio-1,8-naphthyridine (15 g). The product produced by precipitation in water (25 g; m.p. approximately 120° C.) is purified by chromatography on a column 5 cm in diameter containing silica (600 g; 0.063–0.2 mm), eluting with methylene chloride. 100-cc fractions are collected, and fractions 14 to 56 are concentrated to dryness under reduced pressure (4 kPa) to give a solid (22.4 g), m.p. 142–144° C. This product is dissolved in boiling ethanol (250 cc). After 2 hours' cooling at 4° C., the crystallised solid is separated by filtration, washed with ethanol, (2×25 cc) and dried at 40° C. under reduced pressure (0.067 kPa). N-(7-benzylthio-1,8-naphthyridin-2benzamide (19 g) is produced, m.p. 144–145° C.).

2-Amino-7-benzylthio-1,8-naphthyridine can be prepared in the following manner:

To a solution of sodium ethylate prepared from sodium (2.3 g) and ethanol (160 cc), benzyl mercaptan (13.6 g) is added and the mixture is stirred for 1 hour at a temperature in the region of 20° C. 2-Amino-7chloro-1,8-naphthyridine (18 g) is then added and the mixture is heated for 6 hours at 60° C. The suspension produced is poured into water (500 cc) and extracted with methylene chloride (3×250 cc). After being washed with water and dried, the organic solution is concentrated to dryness under reduced pressure (4 kPa) to give 2amino-7-benzylthio-1,8-naphthyridine (15.4 g), m.p. 167° C.

EXAMPLE 11

To a solution of benzoic acid (6.8 g) in anhydrous tetrahydrofuran (180 cc), N,N'-carbonyldiimidazole (9.1 g) is added. Immediate evolution of gas is observed. The mixture is stirred for 2 hours at a temperature in the region of 20° C., until the evolution of gas has ceased. 2-amino-7-phenoxy-1,8-naphthyridine (10 g) is then added and the mixture is heated to reflux for 18 hours.

The mixture is poured into distilled water (800 cc); the precipitate formed is separated by filtration, washed with water and dried in the air.

The product produced (14 g; m.p. 169° C.) is dissolved in boiling acetonitrile (160 cc). After 2 hours' cooling at 4° C., the crystallised solid is separated by filtration, washed with acetonitrile (2×8 cc) and dried at 25° C. under reduced pressure (0.067 kPa). N(7-phenoxy-1,8-naphthyridin-2-yl)benzamide (8 g) is produced, m.p. 170° C. EXAMPLE 12

The procedure is similar to that described in Example 1, but starting with benzoic acid (11 g), N,N'carbonyldiimidazole (16.2 g) and 2-amino-7-(4-methoxyphenoxy)-1,8-naphthyridine (26.7 g). The product produced by precipitation in water (30.8 g; m.p. approximately 110° C.) is dissolved in boiling acetonitrile (150 cc). After 3 hours' cooling at 4° C., the crystallised solid is separated by filtration, washed with acetonitrile (2×5 cc) and dried at 50° C. under reduced pressure (0.067 kPa). N-[7-(4-methoxyphenoxy)-1,8-naphthyridin-2-yl]benzamide (24.7 g) is produced, m.p. 171° C. 2-Amino-7-(4-methoxyphenoxy)-1,8-naphthyridine can be prepared in the following manner:

The procedure is similar to that described in Example 4, but starting with 2-amino-7-chloro-1,8-napthyridine (35.8 g), 4-methoxyphenol (99.2 g) and potassium hydroxide pellets (22.4 g; 85% purity). After treatment with caustic soda and washing, 2-amino-7-(4-methoxyphenoxy)-1,8-naphthyridine (52.9 g) is produced, m.p. 200° C. EXAMPLE 13

The procedure is similar to that described in Example 1, but starting with 2-fluorobenzoic acid (11.2 g), N,N'-carbonyldiimidazole (12.9 g) and 2-amino-7-chloro-1,8-naphthyridine (8.9 g). The product produced by precipitation in water (13.6 g; m.p. 218° C.) is dissolved in boiling 1-propanol (450 cc). After 3 hours' cooling at 4° C., the crystallised solid is separated by filtration, washed with 1-propanol (3×20 cc) and dried at 40° C. under reduced pressure (0.067 kPa). N-(7-chloro-1,8-naphthyridin-2-yl)-2-fluorobenzamide (8.3 g) is produced, m.p. 222° C. EXAMPLE 14

The procedure is similar to that described in Example 1, but starting with 3-fluorobenzoic acid (20 g), N,N'-carbonyldiimidazole (23 g) and 2-amino-7-chloro-1,8-naphthyridine (16.9 g). The product produced by precipitation in water (25 g; m.p. 201° C.) is dissolved in boiling acetonitrile (230 cc). After 4 hours' cooling at 4° C., the crystallised solid is separated by filtration, washed with acetonitrile (2×20 cc) and dried at 40° C. under reduced pressure (0.067 kPa). N-(7-chloro-1,8-naphthyridin-2-yl)-3-fluorobenzamide (21.4 g) is produced, m.p. 202° C. EXAMPLE 15

The procedure is similar to that described in Example 1, but starting with 4-fluorobenzoic acid (11.2 g), N,N'-carbonyldiimidazole (12.9 g) and 2-amino-7-chloro-1,8-naphthyridine (8.9 g). The product produced by precipitation in water (14.3 g; m.p. 230° C.) is dissolved in boiling 2-propanol (800 cc). After 4 hours' cooling at 4° C., the crystallised solid is separated by filtration, washed with 2-propanol (3×10 cc) and dried at 40° C. under reduced pressure (0.067 kPa). N-(7-chloro-1,8-naphthyridin-2-yl)-4-fluorobenzamide (10.3 g) is produced, m.p. 236° C. EXAMPLE 16

The procedure is similar to that described in Example 1, but starting with 4-fluorobenzoic acid (15.4 g), N,N'-carbonyldiimidazole (17.8 g) and 2-amino-7-bromo-1,8-naphthyridine (15.7 g). The product produced by precipitation in water (26.2 g; m.p. 226° C.) is purified by filtration on a column 45 mm in diameter containing silica (300 g; 0.040–0.063 mm), eluting with pure dichloromethane and collecting 100-cc fractions. After concentration to dryness of fractions 10 to 70 at 40° C. under reduced pressure (4 kPa), a solid (18.5 g) is produced, m.p. 228° C. This product is dissolved in boiling ethanol (600 cc). After 2 hours' cooling at 4° C. the crystallised solid is separated by filtration, washed with ethanol (10 cc) and dried at 40° C. under reduced pressure (0.067 kPa). N-(7-bromo-1,8-naphthyridin-2-yl)-4-fluorobenzamide (13.1 g) is produced, m.p. 228° C.

EXAMPLE 17

The procedure is similar to that described in Example 1, but starting with 2,6-difluorobenzoic acid (12.1 g), N,N'-carbonyldiimidazole (12.3 g) and 2-amino-7-chloro-1,8-naphthyridine (8.5 g). The product produced by precipitation in water (6.8 g; m.p. 215° C.) is dissolved in boiling ethanol (450 cc). After 4 hours' cooling at 4° C., the crystallised solid is separated by filtration washed with ethanol (3×15 cc) and dried at 40° C. under reduced pressure (0.067 kPa). N-(7-chloro-1,8-naphthyridin-2-yl)-2,6-difluorobenzamide (7.3 g) is produced, m.p. 242° C.

EXAMPLE 18

The procedure is similar to that described in Example 1, but starting with 2,6-difluorobenzoic acid (5.1 g), N,N'-carbonyldiimidazole (5.2 g) and 2-amino-7-methoxy-1,8-naphthyridine (4.4 g). The product produced by precipitation in water (4.5 g; m.p. 215°–217° C.) is dissolved in boiling ethanol (70 cc). After 1 hour's cooling at 4° C., the crystallised solid is separated by filtration, washed with ethanol (10 cc) and dried at 45° C. under reduced pressure (0.067 kPa). N-(7-methoxy-1,8-naphthyridin-2-yl)-2,6-difluorobenzamide (3.2 g) is produced, m.p. 219°–220° C.

EXAMPLE 19

To a solution of 2-amino-7-methoxy-1,8-naphthyridine (3.5 g) in pyridine (40 cc), 3-acetoxybenzoyl chloride (4.4 g) is added. The mixture is stirred for 1 hour 30 minutes at a temperature in the region of 25° C. The suspension produced is taken up with distilled water (400 cc) and the precipitate produced is dried in the air to give a solid (6.6 g), m.p. 172° C. This product is dissolved in boiling ethanol (140 cc). After 3 hours' cooling at 4° C., the crystallised solid is separated by filtration, washed with ethanol (3×20 cc) and dried at 50° C. under reduced pressure (0.067 kPa). N-(7-methoxy-1,8-naphthyridin-2-yl)-3-acetoxybenzamide (5.3 g) is produced, m.p. 172° C. N-(7-methoxy-1,8-naphthyridin-2-yl)-3-acetoxybenzamide (12 g), produced under the conditions described above, is treated by being heated under reflux for 15 minutes in 10% strength ethanolic caustic potash solution (35 cc). The solid produced after dilution with water (250 cc) acidified with 4N hydrochloric acid (20 cc) is dried in the air to give a solid (9.2 g) melting at a temperature above 260° C. The product produced is dissolved in boiling 1-propanol (1500 cc). After the mixture is cooled for 4 hours at a temperature of 4° C., the crystallised solid is separated by filtration, washed with 1-propanol (3×50 cc) and dried at 60° C. under reduced pressure (0.067 kPa). N-(7-Methoxy-1,8-naphthyridin-2-yl)-3-hydroxybenzamide (6 g) is produced, m.p. 295° C.

EXAMPLE 20

The procedure is similar to that described in Example 1, but starting with 4-methoxybenzoic acid (4.55 g), N,N'-carbonyldiimidazole (6.55 g) and 2-amino-1,8-naphthyridine (5.2 g). The product produced by precipitation in water (8.35 g; m.p. 85° C., viscous) is filtered and then dissolved in boiling 1-propanol (50 cc). After 1 hour's cooling at 4° C., the crystallised solid is separated by filtration, washed with 1-propanol (2×5 cc) and dried at 35° C. under reduced pressure (0.067 kPa). N-(1,8-naphthyridin-2-yl)-4-methoxybenzamide (6.9 g) is produced, m.p. 150° C.

2-Amino-1,8-naphthyridine can be prepared according to U.S. Pat. No. 3,948,917.

EXAMPLE 21

The procedure is similar to that described in Example 1, but starting with 3-methoxybenzoic acid (12.17 g), N,N'-carbonyldiimidazole (12.9 g) and 2-amino-7-chloro-1,8-naphthyridine (8.9 g). The product produced by precipitation in water (15.5 g; m.p. 176° C.) is dissolved in boiling 2-propanol (500 cc). After 2 hours' cooling at 4° C., the crystallised solid is separated by filtration, washed with 2-propanol (3×25 cc) and dried at 40° C. under reduced pressure (0.067 kPa). N-(7-chloro-1,8-naphthyridin-2-yl)-3-methoxybenzamide (11.2 g) is produced, m.p. 178° C.

EXAMPLE 22

The procedure is similar to that described in Example 1, but starting with 4-methoxybenzoic acid (4.6 g), N,N'-carbonyldiimidazole (4.9 g) and 2-amino-7-chloro-1,8-naphthyridine (3.6 g). The product produced by precipitation in water (4.3 g; m.p. 208° C.) is dissolved in boiling acetonitrile (660 cc). After 3 hours' cooling at 4° C., the crystallised solid is separated by filtration, washed with acetonitrile (3×20 cc) and dried at 50° C. under reduced pressure (0.067 kPa). N-(7-chloro-1,8-naphthyridin-2-yl)-4-methoxybenzamide (3.5 g) is produced, m.p. 208° C.

EXAMPLE 23

The procedure is similar to that described in Example 1, but starting with 4-methoxybenzoic acid (10.2 g), N,N'-carbonyldiimidazole (10.8 g) and 2-amino-7-bromo-1,8-naphthyridine (11.2 g). The product produced by precipitation in water (9.8 g; m.p. 220° C.) is dissolved in boiling acetonitrile (1000 cc). After 2 hours' cooling at 4° C., the crystallised solid is separated by filtration, washed with acetonitrile (2×10 cc) and dried at 40° C. under reduced pressure (0.067 kPa). N-(7-bromo-1,8-naphthyridin-2-yl)-4-methoxybenzamide (8.3 g) is produced, m.p. 221° C.

2-Amino-7-bromo-1,8-naphthyridine can be prepared according to the method described by S. CARBONI, Gazz. Chim. Ital. 96, 1464 (1966).

EXAMPLE 24

The procedure is similar to that described in Example 1, but starting with 4-methoxybenzoic acid (12.2 g), N,N'-carbonyldiimidazole (10.3 g) and 2-amino-7-methyl-1,8-naphthyridine (9.5 g). The product produced by precipitation in water (14.4 g; m.p. 110° C.) is dissolved in boiling acetonitrile (150 cc). After 2 hours' cooling at 4° C., the crystallised solid is separated by filtration, washed with acetonitrile (2×10 cc) and dried at 45° C. under reduced pressure (0.067 kPa). N-(7-methyl-1,8-naphthyridin-2-yl)-4-methoxybenzamide (12.7 g) is produced, m.p. 119° C.

2-Amino-7-methyl-1,8-naphthyridine can be prepared according to the method described by E. V. BROWN, J. Org. Chem., 30, 1607 (1965).

EXAMPLE 25

The procedure is similar to that described in Example 1, but starting with 3-methoxybenzoic acid (9.1 g), N,N'-carbonyldiimidazole (9.7 g) and 2-amino-7-methoxy-1,8-naphthyridine (7 g). The product produced by precipitation in water (13 g; m.p. approximately 75° C.) is dissolved in 90 cc of boiling acetonitrile. After 3 hours' cooling at 4° C., the crystallised solid is separated by filtration, washed with acetonitrile (3×10 cc) and dried at 50° C. under reduced pressure (0.067 kPa). N-(7-methoxy-1,8-naphthyridin-2-yl)-3-methoxybenzamide (8.7 g) is produced, m.p. 135° C.).

EXAMPLE 26

The procedure is similar to that described in Example 1, but starting with 4-methoxybenzoic acid (13.2 g), N,N'-carbonyldiimidazole (14.1 g) and 2-amino-7-methoxy-1,8-naphthyridine (11.5 g). The product produced by precipitation in water is dried under reduced pressure (0.067 kPa) and purified by filtration on a column 5 cm in diameter charged with silica (400 g; 0.063–0.2 mm), eluting with methylene chloride.

100-cc fractions are collected. Fractions 8 to 38 are combined and concentrated to dryness under reduced pressure (4 kPa). The product produced is dissolved in boiling acetonitrile (150 cc). After 4 hours' cooling at 4° C. the crystallised solid is separated by filtration, washed with acetonitrile (2×10 cc) and dried at 40° C. under reduced pressure (0.067 kPa).

N-(7-Methoxy-1,8-naphthyridin-2-yl)-4-methoxybenzamide (10.9 g) is produced, m.p. 115° C.

2-Amino-7-methoxy-1,8-naphthyridine can be prepared according to U.S. Pat. No. 3,948,917.

EXAMPLE 27

The procedure is similar to that described in Example 1, but starting with 4-methoxybenzoic acid (19.8 g), N,N'-carbonyldiimidazole (21.1 g) and 2-amino-7-ethoxy-1,8-naphthyridine (18.5 g). The product produced by precipitation in water (28.9 g; m.p. 144° C.) is dissolved in boiling ethanol (280 cc). After 3 hours' cooling at 4° C., the crystallised solid is separated by filtration, washed with ethanol (2×10 cc) and dried at 40° C. under reduced pressure (0.067 kPa). N-(7-ethoxy-1,8-naphthyridin-2-yl)-4-methoxybenzamide (24 g) is produced, m.p. 152° C.

2-Amino-7-ethoxy-1,8-naphthyridine can be prepared according to the method described by S. CARBONI, Gazz. Chim. Ital. 96, 1456 (1966).

EXAMPLE 28

The procedure is similar to that described in Example 1, but starting with 4-methoxybenzoic acid (16.7 g), N,N'-carbonyldiimidazole (19.4 g) and 2-amino-7-isopropoxy-1,8-naphthyridine (25 g). The reaction mixture is poured into water and extracted with ethyl acetate. After concentration to dryness under reduced pressure (4 kPa), the oil produced (39 g) is stirred in the presence of diethyl ether (100 cc) to give a crystallised solid (23 g; m.p. 78° C.). The product produced is dissolved in boiling isopropyl ether (100 cc). After 2 hours' cooling at 4° C., the crystallised solid is separated by filtration, washed with diethyl ether (2×10 cc) and dried at 40° C. under reduced pressure (0.067 kPa). N-(7-isopropoxy-1,8-naphthyridin-2-yl)-4-methoxybenzamide (12.9 g) is produced, m.p. 82° C.

2-Amino-7-isopropoxy-1,8-naphthyridine can be prepared in the following manner:

The procedure is similar to that described in Example 29, but starting with 2-amino-7-chloro-1,8-naphthyridine (35.9 g), 2-propanol (150 cc) and sodium (9.2 g). The excess 2-propanol is evaporated under reduced pressure (4 kPa) and the residue is taken up with distilled water to yield a crystallised solid (38.7 g; m.p. 162° C.). 11 g of the solid produced are dissolved in boiling ethyl acetate (50 cc). After 2 hours' cooling at 4° C., the crystallised solid is separated by filtration, washed with diethyl ether (2×5 cc) and dried at 50° C. under reduced pressure (0.067 kPa). 2-Amino-7-isopropoxy-1,8-naphthyridine (6.9 g) is produced, m.p. 170° C.

EXAMPLE 29

The procedure is similar to that described in Example 1, but starting with 4-methoxybenzoic acid (5.8 g), N,N'-carbonyldiimidazole (6.5 g) and 2-amino-7-(2-methoxyethoxy)-1,8-naphthyridine (8.5 g). The product produced by precipitation in water (8 g; m.p. 75° C., viscous) is purified by chromatography on a column 40 mm in diameter containing silica (250 g; 0.063–0.2 mm), eluting with a mixture (99.5:0.5 by volume) of methylene chloride and methanol. 100-cc fractions are collected, and fractions 12 to 31 are combined and concentrated to dryness under reduced pressure (4 kPa) at 40° C. to give a solid (10.3 g), m.p. 114° C. This product is dissolved in boiling carbon tetrachloride (50 cc). After 16 hours' cooling at 4° C., the crystallised solid is separated by filtration, washed with carbon tetrachloride (2×5 cc) and dried at 40° C. under reduced pressure (0.067 kPa). N-[7-(2-methoxyethoxy)-1,8-naphthyridin-2-yl]-4-methoxybenzamide (8.5 g) is produced, m.p. 114° C.

2-Amino-7-(2-methoxyethoxy)-1,8-naphthyridine can be prepared in the following manner:

The alcoholate of 2-methoxy ethanol is prepared from the corresponding alcohol (100 cc) and sodium (9.2 g). When the evolution of gas has ceased, 2-amino-7-chloro-1,8-naphthyridine (35.9 g) is added and the reaction mixture is stirred at 120° C. for 2 hours 30 minutes, and then poured, after being cooled, into water (100 cc). The solid produced is filtered and dried in the air (30 g; m.p. 175° C.). 10 g of product produced are dissolved in boiling 2-propanol (175 cc). After 3 hours' cooling at 4° C., the crystallised solid is separated by filtration, washed with 2-propanol (10 cc) and dried at 50° C. under reduced pressure (0.067 kPa). 2-Amino-7-(2-methoxyethoxy)-1,8-naphthyridine (8.9 g) is produced, m.p. 176° C.

EXAMPLE 30

The procedure is similar to that described in Example 1, but starting with 4-methoxybenzoic acid (9.6 g), N,N'-carbonyldiimidazole (10.2 g) and 2-allyloxy-7-amino-1,8-naphthyridine (8.5 g). The product produced by precipitation in water (13.9 g; m.p. approximately 70° C.) is purified by chromatography on a column 40 mm in diameter containing silica (250 g; 0.040–0.063 mm), eluting with a mixture (99:1 by volume) of methylene chloride and methanol. 100-cc fractions are collected, and fractions 9 to 23 are combined and concentrated to dryness at 40° C. under reduced pressure (4 kPa) to give a fatty solid (10 g). This product is taken up in isopropyl ether (50 cc). After 30 minutes' stirring at 20°C., the crystallised solid is separated by filtration, washed with isopropyl ether (2×10 cc) and dried at 30° C. under reduced pressure (0.067 kPa). N-(7-allyloxy-1,8-naphthyridin-2-yl)-4-methoxybenzamide (8.9 g) is produced, m.p. 108° C.

2-Allyloxy-7-amino-1,8-naphthyridine can be prepared in the following manner:

The procedure is similar to that described in Example 29, but starting with 2-amino-7-chloro-1,8-naphthyridine (17.9 g), allyl alcohol (75 cc) and sodium (4.6 g).

After the reaction mixture has been poured into water, a crystallised solid (17.6 g) is produced, m.p. 138° C. 7 g of the product obtained are dissolved in boiling carbon tetrachloride (210 cc). After 3 hours' cooling at 4° C., the crystallised solid is separated by filtration, washed with carbon tetrachloride (3×10 cc) and dried at 50° C. under reduced pressure (0.067 kPa). 2-Allyloxy-7-amino-1,8-naphthyridine (6.4 g) is produced, m.p. 138° C.

EXAMPLE 31

The procedure is similar to that described in Example 1, but starting with 4-methoxybenzoic acid (11.5 g), N,N'-carbonyldiimidazole (12 g) and 2-amino-7-propargyloxy-1,8-naphthyridine (10 g). The product produced by precipitation in water (15.3 g; m.p. 140° C.) is dissolved in boiling ethanol (190 cc). After 3 hours' cooling at 4° C., the crystallised solid is separated by filtration, washed with ethanol (3×20 cc) and dried at 50° C. under reduced pressure (0.067 kPa). N-(7-propargyloxy-1,8-naphthyridin-2-yl)-4-methoxybenzamide (10.1 g) is produced, m.p. 140° C.

2-Amino-7-propargyloxy-1,8-naphthyridine can be prepared in the following manner:

The procedure is similar to that described in Example 29, but starting with 2-amino-7-chloro-1,8-naphthyridine (179 g), propargyl alcohol (750 cc) and sodium (46 g). After precipitation in water, the gum produced (120 g) is taken up with stirring in isopropyl ether (500 cc). The solid thus produced (114.5 g; m.p. approximately 150° C.) is purified by chromatography on a column 50 mm in diameter containing silica (1 kg; 0.063–0.2 mm), eluting with methylene chloride and collecting 100-cc fractions (fractions 11 to 20), and then 500-cc fractions (fractions 21 to 26). After concentration to dryness of fractions 6 to 26 under reduced pressure (4 kPa), the residue produced is washed with stirring with ethyl ether, filtered and dried. A solid (21 g) is produced, m.p. 184° C. 10.8 g of this product are dissolved in boiling acetonitrile (100 cc). After 3 hours' cooling at 4° C., the crystallised solid is separated by filtration, washed with acetonitrile (3×20 cc) and dried at 40° C. under reduced pressure (0.067 kPa). 2-Amino-7-propargyloxy-1,8-naphthyridine (6.8 g) is produced.

EXAMPLE 32

The procedure is similar to that described in Example 1, but starting with 4-methoxybenzoic acid (11.8 g), N,N'-carbonyldiimidazole (12.6 g) and 2-amino-7-methylthio-1,8-naphthyridine (9.6 g). The product produced by precipitation in water (15.8 g; m.p. 100° C.) is dissolved in boiling 2-propanol (180 cc). After 1 hour's cooling at 4° C., the crystallised solid is separated by filtration, washed with 2-propanol (10 cc) and then isopropyl ether (2×10 cc), and dried at 40° C. under reduced pressure (0.067 kPa . N-(7-methylthio-1,8-naphthyridin-2-yl)-4-methoxybenzamide (13.6 g) is produced, m.p. 130° C.

2-Methylthio-7-amino-1,8-naphthyridine can be prepared in the following manner:

To a solution, close to saturation, of methyl mercaptan in dimethylformamide (200 cc) maintained at 0° C., sodium hydride (13.3 g) in 50% strength suspension in mineral oil is added in small portions. 2-Amino-7-chloro-1,8-naphthyridine (25 g) is then added to this solution, and the mixture is heated at 100° C. for 2 hours. After being cooled, the reaction mixture is poured into water (500 cc) and extracted with methylene chloride (5×250 cc). The organic extracts are then washed with distilled water (2×200 cc), dried over magnesium sulphate and concentrated to dryness at 40° C. under reduced pressure (4 kPa). The product produced (22.9 g; m.p. 130° C.) is dissolved in boiling ethanol (150 cc). After 2 hours' cooling at 4° C., the crystallised solid is separated by filtration, washed with ethanol (10 cc) and then isopropyl ether (3×10 cc), and dried at 40° C. under reduced pressure (0.067 kPa). 2-Amino-7-methylthio-1,8-naphthyridine (9.6 g) is produced, m.p. 158° C.

EXAMPLE 33

The procedure is similar to that described in Example 1, but starting with 4-methoxybenzoic acid (4.1 g), N,N'-carbonyldiimidazole (4.4 g) and 2-amino-7-phenoxy-1,8-naphthyridine (4.75 g). The product produced by precipitation in water (8.8 g) is purified by chromatography on a column 3 cm in diameter containing silica (140 g; 0.063–0.2 mm), eluting with a mixture (99:1 by volume) of methylene chloride and ethyl acetate. 50-cc fractions are collected, and fractions 7 to 20 are combined and concentrated to dryness at 40° C. under reduced pressure (4 kPa) to give a solid (5.9 g), m.p. approximately 150° C. This product is dissolved in boiling ethanol (70 cc). After 2 hours' cooling at 4° C., the crystallised solid is separated by filtration, washed with ethanol (2×10 cc) and dried at 40° C. under reduced pressure (0.067 kPa). N-(7-phenoxy-1,8-naphthyridin-2-yl)-4-methoxybenzamide (10 g) is produced, m.p. 160° C.

EXAMPLE 34

The procedure is similar to that described in Example 1, but starting with 4-methoxybenzoic acid (6.1 g), N,N'-carbonyldiimidazole (6.5 g) and 2-amino-7-(2-fluorophenoxy)-1,8-naphthyridine (7.65 g). The product produced by precipitation in water (5.5 g; m.p. 200° C.) is dissolved in boiling ethanol (180 cc). After 2 hours' cooling at 4° C., the crystallised solid is separated by filtration, washed with ethanol (2×10 cc) and dried at 40° C. under reduced pressure (0.067 kPa). N-[7-(2-fluorophenoxy)-1,8-naphthyridin-2-yl]-4-methoxybenzamide (3.8 g) is produced, m.p. 208° C.

2-Amino-7-(2-fluorophenoxy)-1,8-naphthyridine can be prepared in the following manner:

The procedure is similar to that described in Example 37, but starting with 2-amino-7-chloro-1,8-naphthyridine (18 g), 2-fluorophenol (44.8 g) and potassium hydroxide pellets (13.2 g; 85% purity). After treatment with caustic soda and washing, the product produced (24 g; m.p. 202° C.) is dissolved in boiling ethanol (200 cc). After 16 hours' cooling at 4° C., the crystallised solid is separated by filtration, washed with ethanol (2×15 cc) and dried at 40° C. under reduced pressure (0.067 kPa). 2-Amino-7-(2-fluorophenoxy)-1,8-naphthyridine (14.9 g) is produced, m.p. 206° C.

EXAMPLE 35

The procedure is similar to that described in Example 1, but starting with 4-methoxybenzoic acid (6.1 g), N,N'-carbonyldiimidazole (6.5 g) and 2-amino-7-(3-fluorophenoxy)-1,8-naphthyridine (7.65 g). The product produced by precipitation in water (14 g) is dissolved in boiling ethanol (110 cc). After 2 hours' cooling at 4° C., the crystallised solid is separated by filtration, washed with ethanol (2×10 cc) and dried at 45° C. at reduced pressure (0.067 kPa). N-[7-(3-fluorophenoxy)-1,8-naphthyridin-2-yl]-4-methoxybenzamide (7 g) is produced, m.p. 151° C.

2-Amino-7-(3-fluorophenoxy)-1,8-naphthyridine can be prepared in the following manner:

The procedure is similar to that described in Example 37, but starting with 2-amino-7-chloro-1,8-naphthyridine (18 g), 3-fluorophenol (44.8 g) and potassium hydroxide pellets (13.2 g; 85% purity). After treatment with caustic soda and washing, the product produced (23.5 g; m.p. 161° C.) is dissolved in boiling acetonitrile (120 cc). After 2 hours' cooling at 4° C., the crystallised solid is separated by filtration, washed with acetonitrile (2×10 cc) and dried at 40° C. under reduced pressure (0.067 kPa). 2-Amino-7-(3-fluorophenoxy)-1,8-naphthyridine (16.5 g) is produced, m.p. 165° C.

EXAMPLE 36

The procedure is similar to that described in Example 1, but starting with 4-methoxybenzoic acid (14.3 g), N,N'-carbonyldiimidazole (15.2 g) and 2-amino-7-(4-fluorophenoxy)-1,8-naphthyridine (15.2 g). The product produced by precipitation in water (22.6 g; m.p. approximately 70° C.) is dissolved in boiling ethanol (130 cc). After 3 hours' cooling at 4° C., the crystallised solid is separated by filtration, washed with ethanol (2×15 cc) and dried at 25° C. under reduced pressure (0.067 kPa). N-[7-(4-fluorophenoxy)-1,8-naphthyridin-2-yl]-4-methoxybenzamide (17 g) is produced, m.p. 100° C.

2-Amino-7-(4-fluorophenoxy)-1,8-naphthyridine can be prepared in the following manner:

The procedure is similar to that described in Example 4, but starting with 2-amino-7-chloro-1,8-naphthyridine (17.9 g), 4-fluorophenol (44.8 g) and potassium hydroxide pellets (13.2 g; 85% purity). After 2 hours' heating at 115° C. and treatment as described above in Example 4, 2-amino-7-(4-fluorophenoxy)-1,8-naphthyridine (15.2 g) is produced, m.p. 210° C.

EXAMPLE 37

The procedure is similar to that described in Example 1, but starting with 4-methoxybenzoic acid (16.4 g), N,N'-carbonyldiimidazole (17.5 g) and 2-amino-7-(2-chlorophenoxy)-1,8-naphthyridine (18.5 g). The product produced by precipitation in water (28 g; m.p. approximately 80° C.) is dissolved in boiling ethanol (800 cc). After 15 hours' cooling at 4° C., the crystallised solid is separated by filtration, washed with ethanol (2×20 cc) and dried at 40° C. under reduced pressure (0.067 kPa). N-[7-(2-chlorophenoxy)-1.8-naphthyridin-2-yl]-4-methoxybenzamide (17.8 g) is produced, m.p 190° C.

2-Amino-7-(2-chlorophenoxy)-1,8-naphthyridine can be prepared in the following manner:

A mixture composed of 2-amino-7-chloro-1,8-naphthyridine (17.9 g), 2-chlorophenol (51.4 g) and potassium hydroxide pellets (13.2 g; 85% purity) is heated for 4 hours at 120° C. The mixture produced is poured into 4N caustic soda (100 cc), and the precipitate formed is separated by filtration and washed with water until the pH =7. After being dried at 40°C. under reduced pressure (0.067 kPa), 2-amino-7-(2-chlorophenoxy)-1.8 naphthyridine (20.6 g) is produced, m.p. 166° C.

EXAMPLE 38

The procedure is similar to that described in Example 1, but starting with 4-methoxybenzoic acid (9.7 g), N,N'-carbonyldiimidazole (10.4 g) and 2-amino-7-(2-bromophenoxy)-1,8-naphthyridine (12.4 g). The product produced by precipitation in water (17.6 g; m.p. approximately 70° C.) is purified by chromatography on a column 45 mm in diameter containing silica (250 g; 0.040–0.063 mm), eluting with a mixture (99:1 by volume) of methylene chloride and methanol, and collecting 50-cc fractions. After concentration to dryness of fractions 5 to 17 at 40° C. under reduced pressure (4 kPa), a solid (10.4 g) is produced, m.p. approximately 70° C. This product is dissolved in boiling ethanol (270 cc). After 3 hours' cooling at 4° C., the crystallised solid is separated by filtration, washed with ethanol (2×15 cc) and dried at 40° C. under reduced pressure (0.067 kPa). N-[7-(2-bromophenoxy)-1,8-naphthyridin-2-yl]-4-methoxybenzamide (8.8 g) is produced, m.p. 183° C.

2-Amino-7-(2-bromophenoxy)-1,8-naphthyridine can be prepared in the following manner:

The procedure is similar to that described in Example 4, but starting with 2-amino-7-chloro-1,8-naphthyridine (19.7 g), 2-bromophenol (81.5 g) and potassium hydroxide pellets (15.15 g; 85% purity). After 10 hours' heating at 120° C. and treatment under the conditions described above in Example 4, the product produced (21.5 g; m.p. 160° C.) is purified by chromatography on a column 45 mm in diameter containing silica (300 g; 0.040–0.063 mm), eluting with a mixture (95:5 by volume) of methylene chloride and methanol and collecting 100-cc fractions. After concentration to dryness of the fractions 2 to 10 at 40° C. under reduced pressure (4 kPa), 2-amino-7-(2-bromophenoxy)-1,8-naphthyridine (12.8 g) is produced, m.p. 206° C.

EXAMPLE 39

The procedure is similar to that described in Example 1, but starting with 4-methoxybenzoic acid (15 g), N,N'-carbonyldiimidazole (16 g) and 2-amino-7-(2-methylphenoxy)-1,8-naphthyridine (15.6 g). The product produced by precipitation in water (19 g; m.p. 50° C.) is purified by chromatography on a column 45 mm in diameter containing silica (270 g; 0.040-0.063 mm), eluting with pure dichloromethane. 100-cc fractions are collected. After concentrating to dryness of fractions 3 to 40 under reduced pressure (4 kPa) at 40° C., a solid (14 g) is produced, m.p. approximately 50° C. This product is dissolved in boiling ethanol (120 cc). After 4 hours' cooling at 4° C., the crystallised solid is separated by filtration, washed with ethanol (10 cc) and dried at 40° C. under reduced pressure (0.067 kPa). N-[7-(2-methylphenoxy)-1,8-naphthyridin-2-yl]-4-methoxybenzamide (11.1 g) is produced, m.p. 153° C.

2-Amino-7-(2-methylphenoxy)-1,8-naphthyridine can be prepared in the following manner:

The procedure is similar to that described in Example 4, but starting with 2-amino-7-chloro-1,8-naphthyridine (17.95 g), 2-methylphenol (43.2 g) and potassium hydroxide pellets (13.2 g; 85% purity). After treatment with caustic soda and washing, the product obtained (21.2 g; m.p. 188° C.) is dissolved in boiling acetonitrile (100 cc). After 4 hours' cooling at 4° C., the crystallised solid is separated by filtration, washed with acetonitrile (10 cc) and dried at 40° C. under reduced pressure (0.067 kPa). 2-Amino-7-(2-methylphenoxy)-1,8-naphthyridine (15.6 g) is produced, m.p. 192° C.

EXAMPLE 40

The procedure is similar to that described in Example 1, but starting with 4-methoxybenzoic acid (8.5 g), N,N'-carbonyldiimidazole (9 g) and 2-amino-7-(3-methylphenoxy)-1,8-naphthyridine (9 g). The product produced by precipitation in water (10 g; m.p. 110° C.) is purified by filtration on a column 45 mm in diameter containing silica (150 g; 0.040-0.063 mm), eluting with pure dichloromethane and collecting 100-cc fractions. After concentration to dryness of fractions 1 to 30 at 40° C. under reduced pressure (4 kPa), a solid (9 g) is produced, m.p. 158° C. This product is dissolved in boiling ethanol (120 cc). After 4 hours' cooling at 4° C., the crystallised solid is separated by filtration, washed with ethanol (10 cc) and dried at 40° C. under reduced pressure (0.067 kPa). N-[7-(3-methylphenoxy)-1,8-naphthyridin-2-yl]-4-methoxybenzamide (7.2 g) is produced, m.p. 160° C.

2-Amino-7-(3-methylphenoxy)-1,8-naphthyridine can be prepared in the following manner:

The procedure is similar to that described in Example 4, but starting with 2-amino-7-chloro-1,8-naphthyridine (17.95 g), 3-methylphenol (43.2 g) and potassium hydroxide pellets (13.2 g; 85% purity). After treatment with caustic soda and washing, the product produced (21.6 g; m.p. 148° C.) is dissolved in boiling ethyl acetate (200 cc). After 18 hours' cooling at 4° C., the crystallised solid is separated by filtration, washed with ethyl acetate (10 cc) and dried at 40° C. under reduced pressure (0.067 kPa). 2-amino-7-(3-methylphenoxy)-1,8-naphthyridine (9 g) is produced, m.p. 152° C.

EXAMPLE 41

The procedure is similar to that described in Example 1, but starting with 4-methoxybenzoic acid (16.7 g), N,N'-carbonyldiimidazole (17.8 g) and 2-amino-7-(2,6-dimethylphenoxy)-1,8-naphthyridine (21.2 g). The reaction mixture is poured into water and extracted with methylene chloride. After concentration of the organic phases to dryness under reduced pressure (4 kPa), the solid residue (33 g) is dissolved in boiling acetone (170 cc). After 2 hours' cooling at 4° C., the crystallised solid is separated by filtration, washed with acetone (10 cc) and dried at 40° C. under reduced pressure (0.067 kPa). By recrystallisation of the solid produced (11.5 g; m.p. approximately 100° C.) in acetone (50 cc), N-[7-(2,6-dimethylphenoxy)-1,8-naphthyridin-2-yl]-4-methoxybenzamide (9.1 g) is produced, m.p. 174° C.

2-Amino-7-(2,6-dimethylphenoxy)-1,8-naphthyridine can be prepared in the following manner:

The procedure is similar to that described in Example 4, but starting with 2-amino-7-chloro-1,8-naphthyridine (17.95 g), 2,6-dimethylphenol (48.6 g) and potassium hydroxide pellets (13.2 g; 85% purity). After treatment with caustic soda and washing, the product produced (24.8 g; m.p. 204° C.) is purified by chromatography on a column 45 mm in diameter containing silica (360 g; 0.040–0.063 mm), eluting with pure methylene chloride and collecting 100-cc fractions. After concentration to dryness of fractions 1 to 48 at 40° C. under reduced pressure (4 kPa), 2-amino-7-(2,6-dimethylphenoxy)-1,8 naphthyridine (21.2 g) is produced, m.p. 218° C.

EXAMPLE 42

The procedure is similar to that described in Example 1, but starting with 4-methoxybenzoic acid (10.2 g), N,N'-carbonyldiimidazole (10.9 g) and 2-amino-7-(2-methoxyphenoxy)-1,8-naphthyridine (13.4 g). The product produced by precipitation in water (18 g; m.p. 167° C.) is dissolved in boiling ethanol (400 cc). After 2 hours' cooling at 4° C., the crystallised solid is separated by filtration, washed with ethanol (2×10 cc) and dried at 45° C. under reduced pressure (0.067 kPa). N-[7-(2-methoxyphenoxy)-1,8-naphthyridin-2-yl]-4-methoxybenzamide (14 g) is produced, m.p. 168°–170° C.

EXAMPLE 43

The procedure is similar to that described in Example 1, but starting with 4-methoxybenzoic acid (15.9 g), N,N'-carbonyldiimidazole (17 g) and 2-amino-7-(3-methoxyphenoxy)-1,8-naphthyridine (17.7 g). The product produced by precipitation in water (12.1 g; m.p. 148° C.) is purified by filtration on a column 45 mm in diameter containing silica (180 g; 0.040–0.063 mm), eluting with pure dichloromethane and collecting 100-cc fractions. After concentration to dryness of fractions 1 to 50 at 40° C. under reduced pressure (4 kPa), a solid (10 g) is produced, m.p. 148° C. This product is dissolved in boiling ethanol (130 cc). After 18 hours' cooling at 4° C., the crystallised solid is separated by filtration, washed with ethanol (10 cc) and dried at 40° C. under reduced pressure (0.067 kPa). N [7-(3-methoxyphenoxy)-1,8-naphthyridin-2-yl]-4-methoxybenzamide (9 g) is produced, m.p. 150° C.

2-Amino-7-(3-methoxyphenoxy)-1,8-naphthyridine can be prepared in the following manner:

The procedure is similar to that described in Example 4, but starting with 2-amino-7-chloro-1,8-naphthyridine (17.95 g), 3-methoxyphenol (49.6 g) and potassium hydroxide pellets (13.2 g; 85% purity). After treatment with caustic soda and washing, the product produced (23.8 g; m.p. 156° C.) is dissolved in boiling ethanol (200 cc). After 18 hours' cooling at 4° C., the crystallised solid is separated by filtration, washed with ethanol (10 cc) and dried at 40° C. under reduced pressure (0.067 kPa). 2-Amino-7-(3-methoxyphenoxy)-1,8-naphthyridine (17.7 g) is produced, m.p. 160° C.

EXAMPLE 44

The procedure is similar to that described in Example 1, but starting with 4-methoxybenzoic acid (9.5 g), N,N'-carbonyldiimidazole (10.2 g) and 2-amino-7-(4-methoxyphenoxy)-1,8-naphthyridine (10.7 g). The product produced by precipitation in water (14.3 g; m.p. 106° C.) is purified by chromatography on a column 35 mm in diameter containing silica (200 g; 0.040–0.063 mm), eluting with a mixture (98:2 by volume) of methylene chloride and methanol and collecting 50-cc fractions. Fractions 22 to 28 are concentrated to dryness under reduced pressure (4 kPa) to give a solid (10.8 g), m.p. 150° C. This product is dissolved in boiling ethanol (250 cc). After 3 hours' cooling at 4° C., the crystallised solid is separated by filtration, washed with ethanol (2×10 cc) and dried at 40° C. under reduced pressure (0.067 kPa). N-[7-(4-methoxyphenoxy)-1,8-naphthyridin-2-yl]-4-methoxybenzamide (9 g) is produced, m.p. 163° C.

EXAMPLE 45

The procedure is similar to that described in Example 1, but starting with 4-methoxybenzoic acid (3.6 g), N,N'-carbonyldiimidazole (4.05 g) and 2-amino-7-(3-pyridyl)oxy-1,8-naphthyridine (6.5 g). The product produced by precipitation in water (3.9 g; m.p. approximately 110° C.) is purified by chromatography on a column 25 mm in diameter containing silica (80 g; 0.040–0.063 mm), eluting with methylene chloride and collecting 50-cc fractions. Fractions 16 to 28 are combined and concentrated to dryness under reduced pressure (4 kPa) to lead to a crystallised solid (3.2 g), m.p. 174° C. The isolated product is dissolved in boiling ethyl acetate (125 cc). After 2 hours' cooling at 4° C., the crystallised solid is separated by filtration, washed with ethyl acetate (2×3 cc) and dried at 50° C. under reduced pressure (0.067 kPa). N-[7-(3-pyridyl)oxy-1,8-naphthyridin-2-yl]-4-methoxybenzamide (2.5 g) is produced, m.p. 184° C.

2-Amino-7-(3-pyridyl)oxy-1,8-naphthyridine can be prepared in the following manner:

The procedure is similar to that described in Example 4, but starting with 2-amino-7-chloro-1,8-naphthyridine (17.9 g), 3-hydroxypyridine (38 g) and potassium hydroxide pellets (11,2 g; 85% purity). The product produced by precipitation in water and extraction with ethyl acetate (4.7 g) is dissolved in boiling ethyl acetate (80 cc). After 3 hours' cooling at 4° C., the crystallised solid is separated by filtration, washed with ethyl ether (2×5 cc) and dried in the air at 20° C. 2-Amino-7-(3-pyridyl)oxy-1,8-naphthyridine (2.1 g) is produced, m.p. 178° C.

EXAMPLE 46

The procedure is similar to that described in Example 1, but starting with 4-methoxybenzoic acid (4.6 g), N,N'-carbonyldiimidazole (4.9 g) and 2-amino-7-(1-methyl-4-piperidyl)oxy-1,8-naphthyridine (5.1 g). The product produced by precipitation in water (6.5 g; m.p. approximately 80° C.) is dissolved in methylene chloride (100 cc), the product is extracted with 2N hydrochloric acid (100 cc), and the aqueous phase obtained is washed with methylene chloride (2×50 cc) and neutralised with 4N caustic soda (50 cc) in the presence of methylene chloride (100 cc). After being washed with water and dried, the organic phase is concentrated to dryness at 40° C. under reduced pressure (4 kPa) to give an amorphous product (6.3 g). This product is dissolved in boiling methylcyclohexane (50 c.). After 1 hour's cooling at 20° C., the crystallised solid is separated by filtration, washed with methylcyclohexane (20 cc) and dried at 50° C. under reduced pressure (0.067 kPa). N-[7-(1-methyl-4-piperidyl)oxy-1,8-naphthyridin-2-yl]-4-methoxybenzamide (5.6 g) is produced, m.p. 200° C.

2-Amino-7-(1-methyl-4-piperidyl)oxy-1,8-naphthyridine can be prepared in the following manner:

The procedure is similar to that described in Example 29, but starting with 2-amino-7-chloro-1,8-naphthyridine (27 g), 4-hydroxy-1-methylpiperidine (71 g) and sodium (8 g). After treatment with water, the reaction mixture is extracted with methylene chloride to give an amorphous solid (33.4 g). This solid is purified by chromatography on a column 60 mm in diameter containing silica (335 g; 0.040–0.063 mm), eluting with a mixture (90:10 by volume) of methylene chloride and methanol, and collecting 100-cc fractions. Fractions 12 to 35 are concentrated to dryness under reduced pressure (4 kPa) to give a solid (10.4 g), m.p. approximately 100° C. This product is dissolved in boiling cyclohexane (50 cc). After 1 hour's cooling at 4° C., the crystallised solid is separated by filtration, washed with cyclohexane (20 cc) and dried at 40° C. under reduced pressure (0.067 kPa). 2-Amino-7-(1-methyl-4-piperidyl)oxy-1,8-naphthyridine (4.3 g) is produced, m.p. 174° C.

EXAMPLE 47

The procedure is similar to that described in Example 1, but starting with 4-ethoxybenzoic acid (13.3 g), N,N'-carbonyldiimidazole (12.9 g) and 2-amino-7-chloro-1,8-naphthyridine (8.9 g). The product produced by precipitation in water (15.3 g; m.p. approximately 170° C.) is dissolved in boiling acetonitrile (500 cc). After 16 hours' cooling at 4° C., the crystallised solid is separated by filtration, washed with acetonitrile (3×25 cc) and dried at 40° C. under reduced pressure (0.067 kPa). N-(7-Chloro-1,8-naphthyridin-2-yl)-4-ethoxybenzamide (8 g) is produced, m.p. 208° C.

EXAMPLE 48

The procedure is similar to that described in Example 1, but starting with 4-ethoxybenzoic acid (8 g), N,N'-carbonyldiimidazole (7.8 g) and 2-amino-7-methoxy-1,8-naphthyridine (5.6 g). The product produced by precipitation in water (9.4 g; m.p. 74° C.) is dissolved in boiling acetonitrile (94 cc). After 3 hours' cooling at 4° C., the crystallised solid is separated by filtration, washed with acetonitrile (3×20 cc) and dried at 30° C. under reduced pressure (0.067 kPa). N-(7-methoxy-1,8-naphthyridin-2-yl)-4-ethoxybenzamide (7 g) is produced, m.p. 145° C.

EXAMPLE 49

The procedure is similar to that described in Example 1, but starting with 4-butoxybenzoic acid (15.5 g), N,N'-carbonyldiimidazole (12.9 g) and 2-amino-7-chloro-1,8-naphthyridine (8.9 g). The product produced by precipitation in water (approximately 18 g; m.p. 140° C.) is purified by chromatography on a column 40 mm in diameter charged with silica (200 g; 0.063–0.2 mm), using methylene chloride as eluant and collecting 60-cc fractions. After concentration to dryness of fractions 8 to 12 at 40° C. under reduced pressure (4 kPa), N-(7-chloro-1,8-naphthyridin-2-yl)-4-butoxybenzamide (6.2 g) is produced, m.p. 197° C.

EXAMPLE 50

The procedure is similar to that described in Example 1, but starting with 3,4-methylenedioxybenzoic acid (16.6 g), N,N'-carbonyldiimidazole (16.2 g) and 2-amino-7-chloro-1,8-naphthyridine (11.7 g). The product produced by precipitation in water (15.7 g; m.p. 256° C.) is dissolved in 1-propanol (1000 cc). After 16 hours' cooling at 4° C., the crystallised solid is separated by filtration, washed with 1-propanol (3×20 cc) and dried at 40° C. under reduced pressure (0.067 kPa). N-(7-chloro-1,8-naphthyridin-2-yl)-3,4-methylenedioxybenzamide (8.4 g) is produced, m.p. 256° C.

EXAMPLE 51

The procedure is similar to that described in Example 1, but starting with 3-dimethylaminobenzoic acid (6.6 g), N,N'-carbonyldiimidazole (6.5 g) and 2-amino-7-chloro-1,8-naphthyridine (5.4 g). The product produced by precipitation in water (9 g; m.p. 212° C.) is dissolved in boiling acetonitrile (400 cc). After 3 hours' cooling at 4° C., the crystallised solid is separated by filtration, washed with acetonitrile (3×20 cc) and dried at 40° C. under reduced pressure (0.067 kPa). N-(7-Chloro-1,8-naphthyridin-2-yl)-3-dimethylaminobenzamide (6.2 g) is produced, m.p. 215° C.

EXAMPLE 52

The procedure is similar to that described in Example 1, but starting with 3-dimethylaminobenzoic acid (18.6 g), N,N'-carbonyldiimidazole (17.8 g) and 2-amino-7-methoxy-1,8-naphthyridine (12.3 g). The product produced by precipitation in water (24.7 g; m.p. 82°–84° C.) is purified by chromatography on a column 4.5 cm in diameter containing silica (220 g; 0.040–0.063 mm), eluting with a mixture (98:2 by volume) of dichloromethane and methanol. 100-cc fractions are collected, and fractions 7 to 22 are combined and concentrated to 40° C. under reduced pressure (4 kPa) to give a solid (24 g), m.p. 90° C. This product is dissolved in boiling acetonitrile (120 cc). After 1 hour's cooling at 4° C., the crystallised solid is separated by filtration, washed with isopropyl ether (2×10 cc) and dried at 40° C. under reduced pressure (0.5 mm Hg). N-(7-methoxy-1,8-naphthyridin-2-yl)-3-dimethylaminobenzamide (5.7 g) is produced, m.p. 130° C.

EXAMPLE 53

The procedure is similar to that described in Example 1, but starting with 3-dimethylaminobenzoic acid (23.1 g), N,N'-carbonyldiimidazole (22.7 g) and 2-amino-7-phenoxy-1,8-naphthyridine (23.7 g). The product produced by precipitation in water (44 g; m.p. approximately 90° C.) is dissolved in boiling acetonitrile (1000 cc). After 3 hours' cooling at 4° C., the crystallised solid is separated by filtration, washed with acetonitrile (3×50 cc) and dried at 40° C. under reduced pressure (0.067 kPa). N-(7-Phenoxy-1,8-naphthyridin-2-yl)-3-

EXAMPLE 54

The procedure is similar to that described in Example 1, but starting with nicotinic acid (3.7 g), N,N'-carbonyldiimidazole (4.9 g) and 2-amino-7-chloro-1,8-naphthyridine (3.6 g). The product precipitated in the mixture is separated by filtration, washed with tetrahydrofuran (3×20 cc) and water (3×50 cc), and is then dried at 50° C. under reduced pressure (0.067 kPa). The product produced (4.75 g; m.p. 200° C.) is dissolved in boiling acetonitrile (435 cc). After 2 hours' cooling at 4° C., the crystallised solid is separated by filtration, washed with acetonitrile (3×20 cc) and dried at 50° C. under reduced pressure (0.067 kPa). N-(7-chloro-1,8-naphthyridin-2-yl)-3-pyridylcarboxamide (3.9 g) is produced, m.p. 200° C.

EXAMPLE 55

The procedure is similar to that described in Example 1, but starting with nicotinic acid (7.4 g), N,N'-carbonyldiimidazole (9.7 g) and 2-amino-7-methoxy-1,8-naphthyridine (7 g). After filtration, washing with water and drying, the crystallised solid formed during the reaction (10.3 g; m.p. 245° C.) is dissolved in boiling 1-propanol (900 cc). After being cooled for 3 hours at 4° C., the crystallised solid is separated by filtration, washed with 1-propanol (3×20 cc) and dried at 50° C. under reduced pressure (0.067 kPa). N-(7-methoxy-1,8-naphthyridin-2-yl)-3-pyridylcarboxamide (8.7 g) is produced, m.p. 247° C.

EXAMPLE 56

The procedure is similar to that described in Example 1, but starting with 6-methoxypyridine-3-carboxylic acid (1.7 g), N,N'-carbonyldiimidazole (1.8 g) and 2-amino-7-chloro-1,8-naphthyridine (1.95 g). The product produced (2.5 g; m.p. 270° C.) is dissolved in a dimethylformamide/methanol (1:6) mixture (190 cc).

After 1 hour's cooling at 4° C., the crystallised solid is separated by filtration, washed with methanol (2×10 cc) and dried at 40° C. under reduced pressure (0.066 kPa). N-(7-chloro-1,8-naphthyridin-2-yl)-6-methoxypyridine-3-carboxamide (2.1 g) is produced, m.p. 270° C.

6-Methoxypyridine-3-carboxylic acid can be prepared in the following manner:

To a suspension of 6-chloropyridine-3-carboxylic acid (4.15 g) in methanol (40 cc), 4 M methanolic sodium methylate solution (40 cc) is added. The mixture is heated under reflux for 60 hours. The solvent is distilled off under reduced pressure (4 kPa). The residue is taken up in distilled water (100 cc) and the mixture is acidified to pH 5 with hydrochloric acid in 11.9 M aqueous solution. The precipitate produced is separated by filtration, washed with distilled water (5×10 cc) and dried in the air. 6-Methoxypyridine-3-carboxylic acid (3.3 g) is produced, m.p. 180° C.

EXAMPLE 57

The procedure is similar to that described in Example 1, but starting with 6-methoxypyridine-3-carboxylic acid (4.7 g), N,N'-carbonyldiimidazole (4.9 g) and 2-amino-7-phenoxy-1,8-naphthyridine (9.1 g). The product produced by precipitation in water (11 g; m.p. 115° C.) is dissolved in boiling acetonitrile (50 cc). After 10 hours' cooling at 20° C., the crystallised solid is separated by filtration, washed with diisopropyl ether (3×10 cc) and dried at 30° C. under reduced pressure (0.067 kPa). N-(7-Phenoxy-1,8-naphthyridin-2-yl)-6-methoxypyridine-3-carboxamide (7 g) is produced, m.p. 115°–120° C.

EXAMPLE 58

The procedure is similar to that described in Example 1, but starting with 2-thiophenecarboxylic acid (9 g), N,N'-carbonyldiimidazole (11.3 g) and 2-amino-7-chloro-1,8-naphthyridine (9.5 g). The product produced by precipitation in water (9.6 g; m.p. 242° C.) is dissolved in boiling ethanol (700 cc). After 1 hour's cooling at 4° C., the crystallised solid is separated by filtration, washed with ethanol (2×25 cc) and dried at 40° C. under reduced pressure (0.067 kPa). N-(7-Chloro-1,8-naphthyridin-2-yl)-2-thiophenecarboxamide (7.5 g) is produced, m.p. 244° C.

EXAMPLE 59

The procedure is similar to that described in Example 1, but starting with 3-thiophenecarboxylic acid (16 g), N,N'-carbonyldiimidazole (20.1 g) and 2-amino-7-chloro-1,8-naphthyridine (16.8 g). The product produced by precipitation in water (10.6 g; m.p. 250° C.) is dissolved in boiling acetonitrile (980 cc). After 2 hours' cooling at 4° C., the crystallised solid is separated by filtration, washed with acetonitrile (2×25 cc) and dried at 40° C. under reduced pressure (0.067 kPa). N-(7-Chloro-1,8-naphthyridin-2-yl)-3-thiophenecarboxamide (7.5 g) is produced, m.p. 254° C.

EXAMPLE 60

The procedure is similar to that described in Example 1, starting with 2-thiophenecarboxylic acid (14 g) N,N'-carbonyldiimidazole (17.8 g) and 2-amino-7-methoxy-1,8-naphthyridine (12.3 g). The product produced by precipitation in water (19.5 g; m.p. 216° C.) is dissolved in boiling ethanol (750 cc). After 3 hours' cooling at 4° C., the crystallised solid is separated by filtration, washed with ethanol (2×25 cc) and dried at 40° C. under reduced pressure (0.067 kPa). N-(7-methoxy-1,8-naphthyridin-2-yl)-2-thiophenecarboxamide (15.6 g) is produced, m.p. 220° C.

EXAMPLE 61

The procedure is similar to that described in Example 1, but starting with 2-thiophenecarboxylic acid (4 g), N,N'-carbonyldiimidazole (5.1 g) and 2-amino-7-chloro-1,8-naphthyridine (7 g). The product produced by precipitation in water (8.8 g; m.p. 175° C.) is dissolved in boiling methanol (150 cc). After 3 hours' cooling at 4° C., the crystallised solid is separated by filtration, washed with methanol (3×10 cc) and dried at 40° C. under reduced pressure (0.067 kPa). N-(7-phenoxy-1,8-naphthyridin-2-yl)-2-thiophenecarboxamide (6 g) is produced, m.p. 176° C.

EXAMPLE 62

The procedure is similar to that described in Example 1, but starting with 3-thiophenecarboxylic acid (5 g), N,N'-carbonyldiimidazole (6.3 g) and 2-amino-7-phenoxy-1,8-naphthyridine (8.3 g). The product produced by precipitation in water (11.6 g; m.p. 110° C.) is dissolved in boiling acetonitrile (50 cc). After 2 hours' cooling at 4° C., the crystallised solid is separated by filtration, washed with diisopropyl ether (3×10 cc) and dried at 35° C. under reduced pressure (0.067 kPa).

N-(7-Phenoxy-1,8-naphthyridin-2-yl)-3-thiophenecarboxamide (8.2 g) is produced, m.p. 95° C.

EXAMPLE 63

The procedure is identical to that described in Example 1, but starting with 5-methylthiophene-2-carboxylic acid (4.1 g), N,N'-carbonyldiimidazole (5.6 g) and 2-amino-7-chloro-1,8-naphthyridine (4.85 g). The product produced (3.8 g; m.p. 220° C.) is dissolved in boiling acetonitrile (150 cc). After 4 hours' cooling at 4° C., the crystallised solid is separated by filtration, washed with acetonitrile (2×10 cc) and dried at 40° C. under reduced pressure (0.066 kPa). N-(7-Chloro-1,8-naphthyridin-2-yl)-5-methylthiophene-2-carboxamide (3.1 g) is produced, m.p. 222° C.

EXAMPLE 64

The procedure is similar to that described in Example 1, but starting with 2-furancarboxylic acid (8.95 g), N,N'-carbonyldiimidazole (12.8 g) and 2-amino-7-methoxy-1,8-naphthyridine (10.5 g). The product produced by precipitation in water (15.5 g; m.p. 199° C.) is dissolved in boiling ethanol (500 cc). After 2 hours' cooling at 4° C., the crystallised solid is separated by filtration, washed with ethanol (2×10 cc) and dried at 45° C. under reduced pressure (0.067 kPa). N-(7-Methoxy-1,8-naphthyridin-2-yl)-2-furancarboxamide (13.5 g) is produced, m.p. 201° C.

EXAMPLE 65

The procedure is similar to that described in Example 1, but starting with 2-furancarboxylic acid (7.5 g), N,N'-carbonyldiimidazole (10.9 g) and 2-amino-7-phenoxy-1,8-naphthyridine (11.9 g). The product produced by precipitation in water (15.7 g; m.p. 164° C.) is dissolved in boiling ethanol (200 cc). After 2 hours' cooling at 4° C., the crystallised solid is separated by filtration, washed with ethanol (15 cc) and dried at 40° C. under reduced pressure (0.067 kPa). N-(7-Phenoxy-1,8-naphthyridin-2-yl)-2-furancarboxamide (14.4 g) is produced, m.p. 167° C.

EXAMPLE 66

The procedure is similar to that described in Example 1, but starting with 3-furancarboxylic acid (7.5 g), N,N'-carbonyldiimidazole (10.9 g) and 2-amino-7-phenoxy-1,8-naphthyridine (11.9 g). The product produced by precipitation in water (13 g; m.p. approximately 90° C.) is dissolved in boiling acetonitrile (80 cc). After 2 hours' cooling at 4° C., the crystallised solid is separated by filtration, washed with acetonitrile (2×10 cc) and dried at 40° C. under reduced pressure (0.067 kPa). N-(7-Phenoxy-1,8-naphthyridin-2-yl)-3-furancarboxamide (10.7 g) is produced, m.p. 102° C.

EXAMPLE 67

To a solution of 6-methylpyridazine-3-carboxylic acid (12 g) in anhydrous tetrahydrofuran (250 cc), N,N'-carbonyldiimidazole (20 g) is added. Slow evolution of a gas is observed. The mixture is stirred at a temperature in the region of 20° C. until evolution of gas has ceased. 2-Amino-7-chloro-1,8-naphthyridine (11 g) is then added and the mixture is heated under reflux for 20 hours. The precipitate produced is separated by filtration, washed with ethanol, dried in the air and then extracted with isopropanol (1000 cc) under reflux in a solid-liquid extractor for 20 hours. After the isopropanol solution thus obtained has been cooled for 2 hours at 4° C., the crystallised solid is separated by filtration and then dissolved in hot (120° C.) dimethylformamide (300 cc).

After 3 hours' cooling at 4° C., the crystallised solid is separated by filtration, washed with methanol (2×20 cc) and dried at 40° C. under reduced pressure (0.066 kPa). N-(7-Chloro-1,8-naphthyridin-2-yl)-6-methylpyridazine-3-carboxamide (4.5 g) is produced, m.p. 258° C.

EXAMPLE 68

The procedure is similar to that described in Example 8, but starting with 2-amino-7-chloroquinoline (10.7 g) in anhydrous pyridine (120 cc) and benzoyl chloride (15.5 g). The product produced by precipitation in water (16 g; m.p. 127° C.) is isolated by filtration and dissolved in boiling cyclohexane (1000 cc). After 1 hour's cooling at 4° C., the crystallised solid is separated by filtration and dried at 45° C. under reduced pressure (0.067 kPa). A product (12.9 g), m.p. 130° C., is produced which is again crystallised in boiling acetone (60 cc). After 1 hour's cooling at 4° C., the recrystallised solid is separated by filtration, washed with acetone (2×5 cc) and dried at 40° C. under reduced pressure (0.067 kPa). N-(7-Chloro-2-quinolyl)benzamide (9 g) is produced, m.p. 133° C.

EXAMPLE 69

To a solution of N-(7-formyl-1,8-naphthyridin-2-yl)-4-methoxybenzamide (6.65 g) in methanol (150 cc), sodium borohydride (0.41 g) is added during 15 minutes at 20° C., and the mixture is left stirred for 1 hour at 20° C. until the evolution of gas has ceased. The suspension produced is poured into distilled water (800 cc) which is acidified to pH 4 with acetic acid. The solid obtained by filtration and drying (6.15 g; m.p. 212° C.) is dissolved in boiling dioxane (180 cc). After the mixture has been cooled for 3 hours at a temperature in the region of 20° C., the crystallised solid is separated by filtration, washed with dioxane (2×15 cc) and dried at 50° C. under reduced pressure (0.067 kPa). N-(7-Hydroxymethyl-1,8-naphthyridin-2-yl)-4-methoxybenzamide (4.4 g) is produced, m.p. 218° C.

N-(7-Formyl-1,8-naphthyridin-2-yl)-4-methoxybenzamide can be prepared in the following manner:

To a solution of N-(7-methyl-1,8-naphthyridin-2-yl)-4-methoxybenzamide (29.3 g) in dioxane (1000 cc), selenium oxide (33.1 g) is added and the mixture is then heated for 3 hours under reflux. The suspension produced is filtered hot, and the filtrate is taken up in methylene chloride (2500 cc) and washed with distilled water (5×1000 cc). The organic solution is dried and concentrated to dryness under reduced pressure (4 kPa) to give a product (11.1 g), m.p. 190° C., which is dissolved in boiling acetonitrile (500 cc). After the mixture has been cooled for 2 hours at 4° C., the crystallised solid is separated by filtration, washed with acetonitrile (2×25 cc) and dried at 50° C. under reduced pressure (0.067 kPa). N-(7-Formyl-1,8-naphthyridin-2-yl)-4-methoxybenzamide (6.65 g) is produced, m.p. 194° C.

EXAMPLE 70

To a solution of 2-chloro-7-phenoxycarbonylamino-1,8-naphthyridine (15 g) in anhydrous tetrahydrofuran (500 cc), anhydrous acetonitrile (500 cc) and 1,2,5,6-tetrahydropyridine (4.2 g) are added. The mixture is heated under reflux for 45 minutes. The solution is concentrated under reduced pressure (4 kPa) to a volume of 100 cc. After 2 hours' cooling at 4° C., the crystallised solid is separated by filtration, washed with acetonitrile (3×15 cc) and dried at 40° C. under reduced pressure (0.067 kPa). N-(7-Chloro-1,8-naphthyridin-2-yl)-1,2,5,6-tetrahydropyridine-1-carboxamide (10.5 g) is produced, m.p. 173° C.

2-Chloro-7-phenoxycarbonylamino-1,8-naphthyridine can be prepared in the following manner:

To a solution of 2-amino-7-chloro-1,8-naphthyridine (9.2 g) in pyridine (130 cc), maintained at a temperature in the region of 20° C., phenyl chloroformate (9.6 g) is added during 15 minutes. The mixture is stirred for 3 hours at a temperature in the region of 20° C. The mixture is poured into distilled water (1000 cc). The precipitate formed is separated by filtration and washed with water.

The product produced (25 g; m.p. approximately 200° C.) is dissolved in boiling acetonitrile (500 cc). After 3 hours cooling at 4° C., the crystallised solid is separated by filtration, washed with acetonitrile (3×50 cc) and dried at 40° C. under reduced pressure (0.067 kPa). 2-Chloro-7-phenoxycarbonylamino-1,8-naphthyridine (7.4 g) is produced, m.p. 208° C.

The present invention also provides pharmaceutical compositions comprising the products of formula (I) in association with a compatible and pharmaceutically acceptable diluent or adjuvant, including coating. These compositions can be used orally, rectally, parenterally or percutaneously.

As solid compositions for oral administration, tablets, pills, powders (generally in gelatine capsules) or granules can be used. In these compositions, the active product according to the invention is mixed with one or more inert diluents such as sucrose, lactose or starch. These compositions can also contain substances other than diluents, e.g. a lubricant such as magnesium stearate.

As liquid compositions for oral administration, there can be used emulsions which are pharmaceutically acceptable, solutions, suspensions, syrups and elixirs containing inert diluents such as water or liquid paraffin. These compositions can also contain substances other than diluents, e.g. wetting, sweetening or flavouring products.

The compositions according to the invention for parenteral administration can be sterile aqueous or non-aqueous solutions, suspensions or emulsions. As a solvent or vehicle, propylene glycol, a polyethylene glycol, vegetable oils, especially olive oil or injectable organic esters, e.g. ethyl oleate, can be used. These compositions can also contain adjuvants, in particular wetting agents, emulsifiers and dispersing agents. The sterilisation can be accomplished several ways, e.g. using a bacteriological filter, incorporating sterilising agents with the composition, by irradiation or by heating. They can also be prepared in the form of sterile solid compositions which can be dissolved at the time of use in sterile water or any other injectable sterile medium.

The compositions for rectal administration include suppositories which can contain, in addition to the active product, excipients such as cocoa butter or suppository wax.

The compositions for percutaneous administration include creams, pomades, lotions and liniments, in which the active product is combined with liquid or pasty excipients, preferably in combination with a vehicle which promotes percutaneous migration.

The compositions according to the invention are especially useful in human therapy for their anxiolytic, hypnotic, anticonvulsant, antiepileptic and muscle relaxant action, and, where appropriate, for their action against infection and their immuno-restorative action.

In human therapy, doses depend on the effect sought and the duration of treatment; they are generally between 10 and 500 mg per day orally for an adult.

In general, the doctor will determine the dosage which he judges to be most suitable according to the age and weight, and all the other factors specific to the subject to be treated.

The examples which follow illustrate compositions according to the invention.

EXAMPLE A

By the customary technique, tablets are prepared containing a 10 mg dose of active product having the following composition:

| | |
|---|---|
| N—(7-chloro-1,8-naphthyridin-2-yl)-4-methoxybenzamide | 0.010 g |
| starch | 0.200 g |
| precipitated silica | 0.036 g |
| magnesium stearate | 0.004 g |

EXAMPLE B

By the customary technique, tablets are prepared containing a 10 mg dose of active product having the following composition:

| | |
|---|---|
| N—(7-chloro-1,8-naphthyridin-2-yl)-4-fluorobenzamide | 0.010 g |
| starch | 0.200 g |
| precipitated silica | 0.036 g |
| magnesium stearate | 0.004 g |

EXAMPLE C

By the customary technique, tablets are prepared containing a 10 mg dose of active product having the following composition:

| | |
|---|---|
| N—(7-methoxy-1,8-naphthyridin-2-yl) cyclopropanecarboxamide | 0.010 g |
| starch | 0.200 g |
| precipitated silica | 0.036 g |
| magnesium stearate | 0.004 g |

EXAMPLE D

By the customary technique, tablets are prepared containing a 10 mg dose of active product having the following composition:

| | |
|---|---|
| N—(7-methoxy-1,8-naphthyridin-2-yl) 2-thiophenecarboxamide | 0.010 g |
| starch | 0.200 g |
| precipitated silica | 0.036 g |
| magnesium stearate | 0.004 g |

We claim:
1. A substituted amide of the formula:

R—CONH—Het in which R denotes cycloalkyl of 3 to 6 carbon atoms, cyclohexadienyl, phenyl, or phenyl substituted by 1 or 2 fluorine atoms, or by a hydroxy radical, or phenyl substituted at positions 3- or 4- by alkyl or alkyloxy, or at positions 3- and 4- by methylenedioxy, or substituted at position 2- or 3- by dialkylamino; or R denotes 3-pyridyl, alkyloxy-3- pyridyl, thienyl, alkylthienyl, furyl, tetrahydropyridyl, pyridazinyl or alkylpyridazinyl; and Het denotes 1,8-naphthyridin-2-yl, unsubstituted or substituted at position 7- by halogen, hydroxymethyl, alkyl, alkyloxy, alkyloxyalkyloxy, alkenyloxy of 3 to 4 carbon atoms, alkynloxy of 3 to 4 carbon atoms, alkylthio, benzylthio, phenoxy, phenoxy substituted by fluorine, or by chlorine or bromine at position 2-, or by alkyloxy or by 1 or 2 alkyls, pyridyloxy or alkylpiperidyloxy; and alkyl portions mentioned above are each linear or branched and contain 1 to 4 carbon atoms each.

2. A substituted amide according to claim 1, in which R is cyclopropyl, cyclobutyl, 1,4-cyclohexadien-1-yl, phenyl, phenyl substituted by 1 to 2 fluorine atoms, or by hydroxy, or at position 3- or 4- by alkyl of 1 to 2 carbon atoms or by alkyloxy of 1 to 4 carbon atoms, or at positions 3- and 4- by methylenedioxy, or at position 3- by dimethylamino, or R is 3-pyridyl, 6-alkyloxy-3-pyridyl, thienyl, 5-alkylthienyl, furyl, 3-pyridazinyl, or 6-alkyl-3-pyridzainyl radicals in which the alkyl has 1 or 2 carbon atoms; and Het denotes 1,8-naphthyridin-2-yl, unsubstituted or substituted at position 7- by halogen, hydroxymethyl, alkyl of 1 to 2 carbon atoms, alkylthio of 1 to 2 carbon atoms, alkyloxy of 1 to 4 carbon atoms, alkyloxyalkyloxy of 2 to 4 carbon atoms, alkyloxy, propargyloxy, benzylthio, phenoxy, phenoxy substituted by fluorine, by chlorine or bromine at position 2-, by alkyloxy or by 1 or 2 alkyl of 1 to 2 carbon atoms each, or by 3-pyridyloxy or 1-alkyl-4-piperidyloxy.

3. A substituted amide according to claim 1, in which R is cyclopropyl, 1-4-cyclohexadien-1-yl, phenyl, or phenyl substituted by 1 or 2 fluorine atoms or by hydroxy, or substituted at position 3- or 4- by alkyloxy of 1 or 2 carbon atoms, or at positions 3- and 4- by methylenedioxy, or at position 3- by dimethylamino, or R is 3-pyridyl, 6-alkyloxy-3-pyridyl in which the alkyl portion contains 1 to 2 carbon atoms, thienyl or furyl, and Het denotes 1,8-naphthyridin-2-yl which is unsubstituted or substituted at position 7- by halogen, alkyl, alkyloxy, alkythio of 1 or 2 carbon atoms, alkyloxyalkyloxy of 2 to 4 carbon atoms, allyloxy, phenozy, phenoxy substituted by fluorine, by chlorine or bromine at position 2-, by alkyloxy or by 1 or 2 alkyls of 1 or 2 carbon atoms each, or by 3-pyridyloxy.

4. A substituted amide according to claim 1, in which R is cyclopropyl, phenyl, phenyl substituted at position 3- or 4- by fluorine, or with 2 fluorine atoms or a hydroxy radical, or substituted at position 3- or 4- with methoxy, or R is 6-alkyloxy-3-pyridyl in which the alkyl portion contains 1 or 2 carbon atoms, 2-thienyl or 3-furyl, and Het denotes 1,8-napthyridin-2-yl substituted at position 7- by halogen, methoxy, phenoxy, or phenoxy substituted by fluorine or at position 2- by chlorine or methyl, or at position 2- or 3- by methoxy; or R denotes 1,4-cyclohexadien-1-yl, phenyl substituted at positions 3- and 4- by methylenedioxy or at position 3- by dimethylamino, or 3-pyridyl, and Het denotes 1,8-naphthyridin-2-yl substituted at position 7- by halogen.

5. A substituted amide according to claim 1 which is N-(7-methoxy-1,8-naphthyridin-2-yl) cyclopropanecarboxyamide.

6. A substituted amide according to claim 1 which is N-(7-Chloro-1,8-naphthyridin-2-yl)-4-fluorobenzamide.

7. A substituted amide according to claim 1 which is N-(7-Bromo-1,8-naphthyridin-2-yl)-4-methoxybenzamide.

8. A substituted amide according to claim 1 which is N-(7-Methoxy-1,8-maphthyridin-2-yl)-4-methoxybenzamide.

9. A substituted amide according to claim 1 which is N-(7-Methoxy-1,8-naphthyridin-2-yl)-2-thiophenecarboxamide.

10. Method of treating a subject in whom an anxiolytic, hypnotic, anti-convulsant, anti-epileptic or muscle-relaxant effect is desired, which comprises administering to such subject an effective amount of a compound according to claim 1.

11. A pharmaceutical composition useful as an anxiolytic, hynotic, anti-convulsant, antiepileptic, or muscle relaxant, comprising an effective amount of a compound according to claim 1, in association with a compatible, pharmaceutically acceptable diluent or adjuvant.

* * * * *